(12) United States Patent
Back et al.

(10) Patent No.: US 10,906,857 B2
(45) Date of Patent: Feb. 2, 2021

(54) PROCESS FOR THE CATALYTIC DECARBOXYLATIVE CROSS-KETONIZATION OF ARYL AND ALIPHATIC CARBOXYLIC ACID

(71) Applicant: RHODIA OPERATIONS, Paris (FR)

(72) Inventors: Olivier Back, Lyons (FR); Philippe Marion, Vernaison (FR)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 16/623,100

(22) PCT Filed: Jun. 15, 2018

(86) PCT No.: PCT/EP2018/066030
§ 371 (c)(1),
(2) Date: Dec. 16, 2019

(87) PCT Pub. No.: WO2018/229285
PCT Pub. Date: Dec. 20, 2018

(65) Prior Publication Data
US 2020/0216378 A1    Jul. 9, 2020

(30) Foreign Application Priority Data

Jun. 16, 2017  (EP) ..................... 17305744
Dec. 15, 2017  (EP) ..................... 17306791

(51) Int. Cl.
| C07C 45/48 | (2006.01) |
| C07C 51/00 | (2006.01) |
| C07C 49/76 | (2006.01) |
| C07C 51/265 | (2006.01) |
| C07C 51/38 | (2006.01) |

(52) U.S. Cl.
CPC ............. *C07C 45/48* (2013.01); *C07C 49/76* (2013.01); *C07C 51/265* (2013.01); *C07C 51/38* (2013.01)

(58) Field of Classification Search
CPC ........ C07C 45/48; C07C 51/265; C07C 51/38
See application file for complete search history.

(56) References Cited

U.S. PATENT DOCUMENTS

| 2,620,359 A | 12/1952 | Britton et al. |
| 2,697,729 A | 12/1954 | Ohlson et al. |
| 3,329,723 A | 7/1967 | Muench et al. |
| 8,748,670 B1 | 6/2014 | Dou et al. |
| 8,779,208 B2 | 7/2014 | Barnicki et al. |
| 10,035,746 B2 | 7/2018 | Back et al. |

FOREIGN PATENT DOCUMENTS

| EP | 2468708 A1 | 6/2012 | |
| GB | 1063268 A | 3/1967 | |
| WO | WO-2017137786 A1 * | 8/2017 | ............. C09K 8/524 |
| WO | 2017174417 A1 | 10/2017 | |

OTHER PUBLICATIONS

Franchini et al. Synthesis, structural characterization and biological evaluation of 4'C-methyl- and phenyl-dioxolane pyrimidine and purine nucleosides. Archives of Pharmacal Research, vol. 40, 537-549. (Year: 2017).*
Granito C., et al., "Decarboxylation Studies. II. Preparation of Alkyl Phenyl Ketones", J. Org. Chem., 1963, 28 (3), pp. 879-881.
Goossen, LJ et al., "Catalytic Decarboxylative Cross-Ketonisation of Aryl- and Alkylcarboxylic Acids using Magnetite Nanoparticles", Advanced Synthesis & Catalysis, (2011) vol. 353, Issue 1, pp. 57-63.
Truce, W.E. et al., "Sulfonation of Ketones and Aldehydes", J. Am. Chem. Soc. 1950, vol. 72, 6, pp. 2740-2743.

* cited by examiner

*Primary Examiner* — Sikarl A Witherspoon

(57) ABSTRACT

The present invention pertains to a process for the cross-ketonization (Piria reaction) between an aryl carboxylic acid and an aliphatic carboxylic acid using a metal-based compound and a slight or a moderate excess of aryl carboxylic acid. A good selectivity, up to 99 mol %, can be achieved. The aryl aliphatic ketone can be used for the preparation of surfactants and other downstream products.

10 Claims, No Drawings

PROCESS FOR THE CATALYTIC DECARBOXYLATIVE CROSS-KETONIZATION OF ARYL AND ALIPHATIC CARBOXYLIC ACID

This application is a U.S. national stage entry under 35 U.S.C. § 371 of International Application No. PCT/EP2018/066030 filed Jun. 15, 2018, which claims priority to European applications No. 17305744.9, filed on Jun. 16, 2017 and 17306791.9, filed on Dec. 15, 2017. The entire contents of these applications are explicitly incorporated herein by this reference.

The present invention relates to a process P for the manufacture of aryl aliphatic ketones K through catalytic decarboxylative cross-ketonization of aryl and aliphatic carboxylic acids.

The present invention further relates to a process P' for preparation of end compounds starting from the so-manufactured aryl aliphatic ketones K.

Finally the invention relates to the end compounds susceptible of being prepared by this process P'.

Processes for the decarboxylative cross-ketonisation of aryl carboxylic acids and alkyl carboxylic acids are known in the art. One may refer to the following prior art documents:

U.S. Pat. No. 2,697,729 published in 1954 describes at Example XII the reaction between stearic acid and benzoic acid in a nearly equimolar stoichiometry catalyzed by alumina $Al_2O_3$ in a closed vessel during 4h30 at 350° C. A poor selectivity is obtained. Indeed, only 30% of the product is stearophenone, that is the aryl alkyl ketone, and 45% of the product is stearone, that is the dialkyl ketone.

U.S. Pat. No. 3,329,723 published in 1962 reports the synthesis of cyclohexyl-phenyl ketone through decarboxylative cross-ketonisation between cyclohexanecarboxylic acid and benzoic acid. The cross-ketonisation reaction is mediated by $Mn^{(II)}$ salts. A catalytic molten media is first prepared by reacting at 122° C. at least 1 equivalent of MnO with 2 equivalents of carboxylic acids. The reaction temperature is then increased at 345° C. triggering ketonization. A mixture of carboxylic acids (cyclohexanecarboxylic acid:benzoic acid=1.22:1) is continuously added into the reaction medium under a stream of either hydrogen or steam to keep the catalyst active.

Overall the amount of Mn metal used is around 6 mol % relative to the total amount of carboxylic acids engaged in the reaction.

A very good selectivity of 98% of cyclohexyl-phenyl ketone has been obtained. However, the conversion regarding benzoic acid is 81% and the conversion regarding cyclohexanecarboxylic acid is only 65% according to example 1. Partial conversions of starting acids require tedious work-up that can be costly for industrialization. Furthermore, the necessity to conduct reaction under a stream of hydrogen or steam in combination with high temperature and acidic media is also detrimental for an industrial process. Finally it is specified in the text that "operating according to the same method, but replacing the manganese (II) by iron (II) or cadmium, the mixed ketone is also obtained, but the yields are not quantitative" showing that Mn salts are necessary and iron salts do not give good results. Using toxic Mn salts can be detrimental for industrialization of the process.

The paper entitled "Decarboxylation studies. II Preparation of alkyl phenyl Ketones" published in J. Org. Chem., 28, pp. 879-881, (1963) discloses a cross-ketonization process in which benzoic acid is reacted with an alkyl carboxylic acid in liquid phase in the presence of iron. During the reaction iron salts are first formed from $Fe^{(0)}$ at 250° C. during 45 min and the complexes are decomposed at 280-300° C. during 3 h to form the aryl alkyl ketone. It is worth noting that slight excess of iron is used relative to the total molar quantities of benzoic and aliphatic acids. According to the experimental procedure described in the article, 0.1 mole of benzoic acid, 0.1 mole of aliphatic acid and 0.11 mole of Fe (corresponding to a 10% mol excess) are used. The reaction thus requires a significant amount of iron. It is therefore desirable to find a process which uses lower amount of metal. Furthermore, Table I of this paper shows that the isolated yields of the heavier aryl alkyl ketones (containing between 9 and 17 carbon atoms in their alkyl chain) varies between 50% and 66%. The highest yield is 66% (corresponding to an analyzed crude yield of 78%) which is obtained by reacting benzoic acid with palmitic acid. This paper reports on Table II that using a 4-fold excess of benzoic acid with respect to propanoic acid leads to an isolated yield of 72% of propiophenone. However, in the perspective of an industrial process, using a high excess of a reactant requires additional processing steps to remove and recycle the reactant in excess and therefore add additional costs. The yield drops to only 60% when a 2-fold excess of benzoic acid is used. It is therefore desirable to find a process which allows preparing the aryl alkyl ketone at a higher yield, typically at least 80% and with reduced amounts of metals and limited excess of reactant More recently, a catalytic decarboxylative cross-ketonisation of aryl- and alkyl-carboxylic acids has been described in Adv. Synth. Catal., 353, pp. 57-63, (2011) and in EP-A-2 468 708. Linear aliphatic carboxylic acids are reacted with 3-toluic acid in presence of a magnetite ($Fe_3O_4$) nanopowder. In this study, magnetite is used in catalytic amounts. With this catalyst, the cross-ketonization between m-toluic acid and phenylacetic acid affords a mixture of the desired cross-adduct and 1,3-diphenylacetone (the homo-ketonization product of phenylacetic acid) in a 10:1 ratio with a yield of 80%. Table 3 shows that the reaction may lead to a yield of cross-ketonization product between 74 and 86% using a slight excess of aryl carboxylic acid with respect to the carboxylic acid (1.2:1). Nevertheless, one major drawback of this process is that it involves the use of a nanopowder which can be costly and difficult to handle in case of an implementation at an industrial scale. Besides, the reaction requires using a high boiling point solvent (Dowtherm A) which has then to be removed in a downstream process through distillation. This additional step of solvent removal results in an unecomomical process when run at an industrial scale. Besides, it is to be noted that the reaction time is 21 h, which is very long.

In conclusion, in the above prior art documents, either the metal involved in the decarboxylative cross-ketonisation is employed in a stoichiometric amount (Fe) or is toxic and sensitive requiring complex implementation (e.g. in the case of $Mn^{(II)}$ salts, the use of a stream of hydrogen or $H_2O$ is necessary) or the process requires the use of expensive nanoparticles in combination with a high boiling point solvent. The use of a solvent can be detrimental for industrialization as it results to a lower productivity and because separation of products will require complex and expensive downstream processes, namely distillation of high boiling point compounds. Also, the yields hardly exceed 85% in those studies, and for the Mn mediated ketonization process the reactants conversion is partial requiring costly purification steps. Finally, the product mixture always contains a significant amount of homo-ketonization dialkyl ketones, which will require again additional purification steps.

Therefore, a process is sought which obviates the above-mentioned drawbacks.

Process P for Making Aryl Alkyl Ketones K

Summarized Description of the Process P

It has now been found a new process P for the preparation of aryl aliphatic ketones through catalytic decarboxylative cross-ketonisation of aryl carboxylic acids and aliphatic carboxylic acids. This process P uses a metal in a catalytic amount and allows preparing aryl aliphatic ketones with a high yield, typically at least 70% and up to 99%. A high selectivity in aryl aliphatic ketone may also be obtained, typically at least than 80% and up to 99%.

A first object of the invention is a process P for the catalytic decarboxylative cross-ketonisation of aryl- and aliphatic carboxylic acids comprising the steps of:
a) providing a mixture containing:
  i) an aryl carboxylic acid;
  ii) an aliphatic carboxylic acid;
  iii) a metal-containing compound;
  in which the number of moles of the metal in the mixture is at least equal to 90% of the sum of the number of moles of aryl carboxylic acid and the number of moles of aliphatic carboxylic acid divided by the valency of the metal;
  said mixture being substantially free of any added solvent;
b) heating the mixture at a temperature sufficient to form metal carboxylates;
c) further heating the mixture at a temperature sufficient to form a dialiphatic ketone and an aryl aliphatic ketone;
d) adding to the reaction mixture of step c):
  i) aryl carboxylic acid in an amount which corresponds substantially to the amount of aryl carboxylic acid consumed during the formation of the aryl aliphatic ketone in step c);
  ii) aliphatic carboxylic acid in an amount which corresponds substantially to the amount of aliphatic carboxylic acid consumed during the formation of the aryl aliphatic ketone and the dialiphatic ketone in step c);
  maintaining the mixture at a temperature sufficient to continue forming the dialiphatic ketone and the aryl aliphatic ketone;
e) optionally repeating step d).

According to one embodiment, the mixture substantially free of any added solvent is free of any added solvent (i.e. it is completely free of any added solvent).

According to one embodiment:
x is the number of moles of aryl carboxylic acid,
y is the number of moles of aliphatic carboxylic acid, and the number of moles of a metal of valence z in the mixture of step a) is within the range of from $0.9[(x+y)/z]$ to $1.1[(x+y)/z]$, preferably from $0.95[(x+y)/z]$ to $1.05[(x+y)/z]$, more preferably from $0.98[(x+y)/z]$ to $1.02[(x+y)/z]$, more preferably from $0.99[(x+y)/z]$ to $1.01[(x+y)/z]$.

According to one embodiment, the metal is iron.

According to one embodiment, the iron-containing compound is selected from the group consisting of iron metal, bivalent $Fe^{(II)}$ compounds, trivalent $Fe^{(III)}$ compounds, compounds in which iron is present in both bivalent $Fe^{(II)}$ and bivalent $Fe^{(III)}$ oxidation states, such as magnetite $Fe_3O_4$.

According to one embodiment, step b) is carried out at a temperature $T_1$ from 225° C. to 290° C., preferably from 250° C. to 275° C.

According to one embodiment, step c) and/or step d) is carried out at a temperature $T_2$ from 300° C. to 400° C., preferably from 315° C. to 400° C.

According to one embodiment, the molar ratio of the total amount of aryl carboxylic acid and the aliphatic carboxylic acid ranges from 0.3 to 1.8.

According to one embodiment, heating in step b) is carried out for a duration ranging from 1 to 6 h, preferably for a duration less than or equal to 3 h.

According to one embodiment, heating in step c) is carried out for a duration ranging from 1 to 4 h, preferably for a duration less than or equal to 1.5 h.

According to one embodiment, heating in step d) is carried out for a duration ranging from 1 to 4 h, preferably for a duration less than or equal to 1.25 h.

According to one embodiment, the process P is carried out for a duration less than or equal to 20 hours, preferably for a duration less than or equal to 8 hours.

According to one embodiment, the aryl carboxylic acid is selected from the group consisting of benzoic acid, furoic acid, o-toluic acid, m-toluic acid and p-toluic acid.

According to one embodiment, the aliphatic carboxylic acid is a fatty acid. The fatty acid may contain from 8 to 18 carbon atoms.

Another object of the invention is a process P' for the preparation of at least one end compound from at least one aryl aliphatic ketone, said process P' comprising:

synthesizing the aryl aliphatic ketone through the process P as described above, causing the aryl aliphatic ketone to react in accordance with a single or multiple chemical reaction scheme involving at least one reagent other than the aryl aliphatic ketone, wherein at least one product of the chemical reaction scheme is the end compound that is not further caused to be chemically converted into another compound.

DETAILED DESCRIPTION OF THE PREFERRED EMBODIMENTS

In the following description, the term "yield in ketone" refers to the ratio between the total number of moles of aryl aliphatic ketone plus twice of the total number of moles of dialiphatic ketones produced through the process P of the invention over the overall number of moles of aliphatic carboxylic acid.

The term "selectivity in aryl aliphatic ketone" refers to the ratio between the number of moles of aryl aliphatic ketone produced through the process P of the invention and the number of moles of all the ketones produced (mainly aryl aliphatic ketone and dialiphatic ketone).

The term "aliphatic carboxylic acid" refers to a fatty acid, that is, a monocarboxylic acid having a long aliphatic chain. The aliphatic chain may be linear or branched, saturated or unsaturated. The total number of carbon atoms in the carboxylic fatty acid may vary from 4 to 28. Preferred fatty acids are those containing a number of carbon atoms from 8 to 22 carbon atoms, preferably from 12 to 18 carbon atoms. The most preferred fatty acids are caprylic acid ($C_8$), capric acid (CO, lauric acid ($C_{12}$), myristic acid ($C_{14}$), palmitic acid ($C_{16}$), oleic and stearic acids ($C_{18}$).

The term "aryl carboxylic acid" refers to a monocarboxylic acid comprising a substituent derived from an aromatic ring. The term aromatic ring encompasses also heteroaromatic rings such as furan, pyridine, thiophene etc. Preferred aryl carboxylic acids are selected from the group consisting of benzene monocarboxylic acid (benzoic acid), toluene monocarboxylic acid, xylene monocarboxylic acid, naphthalene monocarboxylic acid and furoic acid. The aromatic ring may contain one or more halogen substituents. The most preferred aryl carboxylic acids are benzoic acid and toluic acid.

A "bivalent metal" refers to a metal capable of forming two chemical bonds with X type ligands (one electron donating neutral ligand). In the same way "trivalent metal" or "tetravalent metal" are metals capable of forming three or four chemical bonds respectively with X type ligands. The preferred metals used in the present invention may be selected from the group consisting of Mg, Ca, Ti, Zr, V, Cr, Mo, W, Mn, Fe, Co, Ni, Cu, Zn, Cd, al, Ga, In, Tl, Ge, Sn, Pb. More preferably, the metal is Fe or Mg.

The process P of the present invention comprises two main steps which are detailed hereafter.

The first step comprises a first phase during which the aryl carboxylic acid, the aliphatic carboxylic acid and the metal-containing compound are reacted to yield a mixture of metal carboxylate complexes (also named metal complexes in the present description). It is essential that no free acids be present after this first step in the reaction mixture. For this reason, the amount of metal-containing compound introduced into the acid mixture is calculated by taking into account the valence state of the metal. For a bivalent metal, the amount of metal introduced must be at least 90% of half of the sum of the number of moles of the aromatic carboxylic acid and the aliphatic carboxylic acid. Let us assume that:

x is the number of moles of the aromatic carboxylic acid;
y is the number of moles of the aliphatic carboxylic acid;
then the number of moles of a bivalent metal should be at least equal to $0.9[(x+y)/2]$.

In one preferred embodiment, the number of moles of a bivalent metal introduced into the acid mixture is at least equal to $(x+y)/2$, preferably it is equal to $(x+y)/2$. For a trivalent metal, the amount of metal introduced must be at least 90% of one third of the sum of the number of moles of the aromatic carboxylic acid and the aliphatic carboxylic acid, that is $0.9[(x+y)/3]$. For a tetravalent metal, the amount of metal introduced will be at least 90% of one fourth of the sum of the aromatic carboxylic acid and the aliphatic carboxylic acid, that is $0.9[(x+y)/4]$. More generally, for metal with a valence state of z, the amount will be at least $0.9[(x+y)/z]$.

In addition, mixture of metals with different valence states can be used. This is the case for example for magnetite $Fe_3O_4$, where there is a mixture of Fe(II) and Fe(III).

In the case of a bivalent metal, the mixture of the aromatic carboxylic acid and the aliphatic carboxylic acid reacts with the bivalent metal to form mainly the following metal carboxylates complexes (I, II and III):

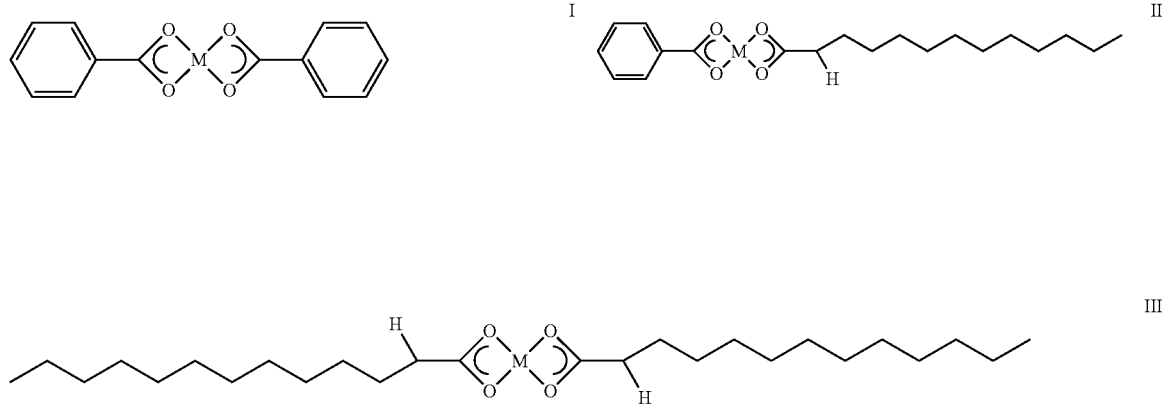

It is essential that all the acids form a complex with the metal.

The first phase of the first step is carried out at a temperature $T_1$ high enough to convert all the acid to carboxylate complexes. The progressive formation of these complexes may be monitored through Fourier Transform InfraRed spectroscopy (FT-IR) so that the skilled person can adjust temperature $T_1$ depending on the desired rate of formation of these three complexes. Generally, $T_1$ ranges from 100° C. to 290° C., preferably from 250 to 275° C.

The first step comprises a second phase in which the temperature is increased at a temperature $T_2$ sufficient to decompose the carboxylate complexes containing at least one aliphatic carboxylate ligand to ketones. In the case of a bivalent metal, the complexes (II) and (III) undergo degradation to ketones: decomposition of the dialiphatic complex (III) leads to the formation of the dialiphatic ketone. Decomposition of the mixed complex (II) leads to the formation of the desired aryl aliphatic ketone. The decomposition of both complexes (II) and (III) releases metal oxide and $CO_2$. It has been observed that complex (I) is stable and does not decompose into a ketone. The decomposition of both complexes (II) and (III) into the aryl aliphatic ketone and the dialiphatic ketone respectively may be schematized as follows:

aliphatic carboxylic acid. Therefore, no new addition of metal-containing compounds is further necessary in the process P.

As in the first step, it is important that no free acids be present in the reaction mixture during the subsequent additions of acids. Consequently, appropriate amounts of aryl carboxylic acid and aliphatic carboxylic acid which are to be added in the second step at each cycle are determined such as to compensate the amount of acids that have been consumed through the formation of ketones from decomposition of intermediately formed complexes (II) and (III) at the end of step 1 or at the end of the previous cycle in step 2. For example, in the case of a bivalent metal, the consumption of acids is caused by the decomposition of complexes (II) and (III). Aliphatic carboxylic acid is added in an amount at each cycle which corresponds substantially to the amount of aliphatic carboxylic acid consumed during the formation of the dialiphatic ketone (2 equivalents of aliphatic carboxylic acid are consumed to form 1 equivalent of dialiphatic ketone) and the aryl aliphatic ketone (1 equivalent of aliphatic carboxylic acid is consumed to form 1 equivalent of aryl aliphatic ketone) in the first step or at the end of the previous cycle in the second step. Therefore in theory, all the aliphatic acid added in the first phase of step 1 or at the beginning of the previous cycle in step 2 has been

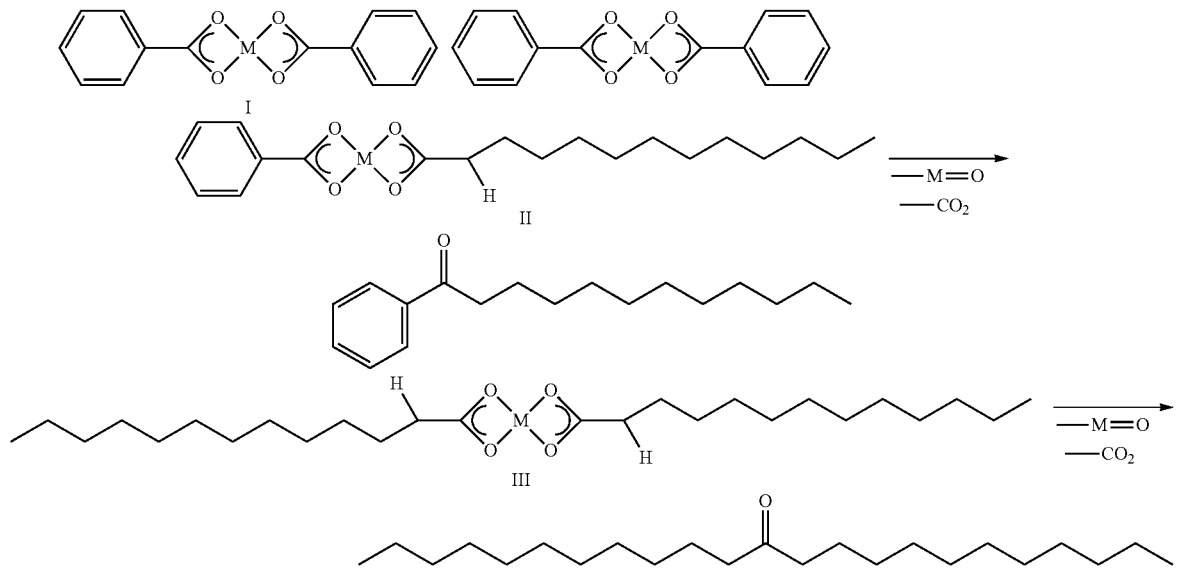

The progressive formation of the ketones may be monitored through Fourier Transform InfraRed spectroscopy (FT-IR) so that the skilled person can adjust temperature $T_2$ depending on the desired rate of formation of the ketones. Generally, $T_2$ ranges from 300 to 400° C., preferably from 315 to 400° C.

The time required for complex decomposition generally ranges from 1 to 3 hours, typically less than or equal to 1h30 min.

The second step of the process P consists in one or several repeated cycles consisting of subsequent additions of the aryl carboxylic acid and the aliphatic carboxylic acid followed by an appropriate reaction time. The aryl carboxylic acid is preferably added before the aliphatic carboxylic acid. It is believed that the metal oxide released by the decomposition of complexes (II) and (III) acts as a catalyst during the subsequent addition(s) of the aryl carboxylic acid and the consumed to ketones. Aryl carboxylic acid is added in an amount which corresponds substantially to the amount of aryl carboxylic acid consumed during the formation of the aryl aliphatic ketone (1 equivalent of aryl carboxylic acid is consumed to form 1 equivalent of aryl aliphatic ketone) in the first step or at the end of the previous cycle. By the term "substantially" it is meant that the amount of each acid added at each cycle can deviate from the number of acid consumed during the first step or the previous cycle by plus or minus 30%, preferably plus or minus 20%, preferably plus or minus 10%, preferably plus or minus 5%, preferably plus or minus 2%.

The Applicant has calculated for various stoichiometries of aliphatic carboxylic acid, aryl carboxylic acid and bivalent metal involved in the preparation of the reaction mixture of the first step, the theoretical number of equivalents of complexes (I), (II) and (III) formed at the end of the first phase of the first stage as well as the mol % of aryl aliphatic complex (II) relative to the sum of complexes (II) and (III). The results of this determination are reproduced in Table 1 below.

TABLE 1

Number of equivalents of the complexes formed for various ratios of reactants involved in the first step of the process P

| | Number of equivalents involved in the first step of the process P | | | Number of equivalents of the complexes formed at stage 1 | | | |
|---|---|---|---|---|---|---|---|
| Condition | x* Aromatic carboxylic acid | y** Aliphatic carboxylic acid | (x + y)/2 (metal) | diaromatic complex (I) | aryl aliphatic complex (II) | dialiphatic complex (III) | mol % of aryl aliphatic complex *** |
| 1 | 0.5 | 1 | 0.75 | 0.08 | 0.33 | 0.33 | 50 |
| 2 | 1 | 1 | 1 | 0.25 | 0.50 | 0.25 | 67 |
| 3 | 1.5 | 1 | 1.25 | 0.45 | 0.60 | 0.20 | 75 |
| 4 | 2 | 1 | 1.5 | 0.67 | 0.67 | 0.17 | 80 |
| 5 | 2.5 | 1 | 1.75 | 0.89 | 0.71 | 0.14 | 83 |
| 6 | 3 | 1 | 2 | 1.13 | 0.75 | 0.13 | 86 |
| 7 | 3.5 | 1 | 2.25 | 1.36 | 0.78 | 0.11 | 88 |
| 8 | 4 | 1 | 2.5 | 1.60 | 0.80 | 0.10 | 89 |
| 9 | 4.5 | 1 | 2.75 | 1.84 | 0.82 | 0.09 | 90 |
| 10 | 5 | 1 | 3 | 2.08 | 0.83 | 0.09 | 91 |

*number of equivalents of aryl carboxylic acid
**number of equivalents of aliphatic carboxylic acid
*** molar fraction of aryl aliphatic complex (II) relative to the sum of aryl aliphatic complex (II) and dialiphatic complex (III).

Assuming that the decomposition rate of complex (II) into the aryl aliphatic ketone is about the same as the decomposition rate of complex (III) into the dialiphatic ketone, one can estimate from the knowledge of the number of moles of complexes (II) and (III) both the number of moles of dialiphatic ketone and the number of moles of aryl aliphatic ketone formed in theory by the ketonization reaction conducted at the end of the second phase in the first step. We can assume that the number of moles of aryl aliphatic ketone will be equal to the number of moles of complex (II) and the number of moles of dialiphatic ketone will be equal to the number of moles of complex (III). Then the amounts of aliphatic and aryl carboxylic acids that need to be added after the first step can be deduced as explained above. As the amounts of carboxylic acids added at each cycle in step 2 is calculated to compensate the amounts of carboxylic acids consumed during the ketonization in the first step or in the previous cycle, it is assumed that at each cycle the ratio of intermediately formed complexes are the same and therefore the amounts of formed ketones are the same. Therefore, the amounts of carboxylic acids added at each cycle in the second step correspond to the amounts of carboxylic acids consumed for the formation of aryl aliphatic and dialiphatic ketones during the second phase of step 1) and is the same during the whole process P. It can be entirely deduced from the table 1 according to the stoichiometry of aryl carboxylic acid and aliphatic carboxylic acid used in the first step. A detailed example of calculation using the data of Table 1 is provided hereafter in relation with Example 1.1.

The fraction of the metal which is part of the complexes (II) and (III) is released during their decomposition into ketones during the second phase of step 1 or at each cycle of step 2. This metal fraction which can be in the form of metal oxide reacts with each subsequently added aryl carboxylic acid and aliphatic carboxylic acid to regenerate the complex (II) and (III) and water as a by-product.

During each cycle, after subsequent addition of aryl carboxylic acid and aliphatic carboxylic acid and formation of the complexes, the reaction mixture is kept at a temperature sufficient to lead again to the formation of the ketones mixture and metal oxide. The temperature at which the reaction mixture is maintained can be the same as the temperature $T_2$ of the second phase of first step. It can also be different. Generally, it is convenient to keep the reaction mixture at a temperature substantially equal to $T_2$, namely $T_2$ plus or minus 10° C.

Generally, the reaction is kept at a temperature of at least 300° C. for a duration ranging from 1 to 3 hours, typically less than or equal to 1 h 15 min.

The number of cycles in the second step is not particularly limited. It is however convenient to perform in the second step from three to five cycles. A higher number of repetition may also be envisaged.

Generally, the cycles in the second step of the process P are repeated until the ratio of the number of moles of metal over the overall number of moles of acids introduced in the reaction mixture from the beginning of the process P is equal to or below 0.25. As explained above, the metal-containing compound is introduced once in the reaction mixture at the beginning of the process P while the two acids are progressively introduced in the reaction mixture during the course of the process P. Thus, during the reaction, the ratio of the number of moles of metal over the overall number of moles of acids introduced in the reaction mixture from the beginning of the process P will decrease.

The first and the second step are typically carried out in an inert atmosphere, for example by circulating a stream of $N_2$ or Ar above the reaction mixture.

Water and carbon dioxide are by-products which are continuously removed from the reaction mixture over the course of the process P.

At the end of the process P, the desired ketone products are separated from the metal oxide and the metal complex (I) thanks to filtration and/or aqueous washing and/or solvent extraction and/or distillation.

The process P of the invention allows preparing an aryl aliphatic ketone with a yield of at least 70%, preferably at least 80%, preferably at least 95% and up to 99%.

The process P of the invention allows preparing an aryl aliphatic ketone with a selectivity of at least 55%, preferably at least 80%, preferably at least 85%, preferably at least 95%.

In one preferred embodiment, the process P of the invention allows preparing an aryl aliphatic ketone with a selectivity of at least 55% for an overall molar ratio of aryl carboxylic acid over aliphatic carboxylic acid not higher than 0.37.

In one preferred embodiment, the process P of the invention allows preparing an aryl aliphatic ketone with a selectivity of at least 85% for a molar ratio of aryl carboxylic acid over aliphatic carboxylic acid not higher than 0.83.

In one preferred embodiment, the process P of the invention allows preparing an aryl aliphatic ketone with a selectivity of at least 99% for a molar ratio of aryl carboxylic acid over aliphatic carboxylic acid not higher than 1.75.

This high selectivity is desirable to reduce manufacturing costs and to decrease complexity of downstream processes.

In addition to obtaining a high selectivity and a high yield, the process P of the invention provides the following advantages:
- it does not require any additional solvent.
- the catalyst does not need to be used in the form of nanoparticles.
- it can be performed in a relatively short reaction times (less than or equal to 10 hours, generally less than or equal to 8 hours, less than or equal to 6 hours).
- it can be conducted at atmospheric pressure.

The aryl aliphatic ketones prepared by the process P of the invention are seen as valuable intermediates to be transformed into new surfactants. They are potential candidates for the replacement of widely used Nonylphenol ethoxylates (NPE). Indeed, nowadays, nonylphenol ethoxylates raise concerns because of their reprotoxicity and also because they are considered as endocrine disruptors.

The aryl aliphatic ketones prepared through the process P of the present invention may be used as reactants in a single or a multiple chemical reaction scheme. The end product may act as an emulsifier, a textile auxiliary, a dyeing additive, a detergent, a dispersant, a softener, a crude oil emulsifier. It may be used in sectors of industry such as detergents, personal care products, textiles, metallurgical industry, paper making, petroleum, pesticides, pharmacy, printing, synthetic rubbers, aqueous emulsions, coatings, inks, glue and plastics.

Process P' for Making End Products from Aryl Aliphatic Ketones

Summarized Description of the Process P'

Aryl aliphatic ketones are versatile starting materials for a wide variety of end products.

It was thus another object of the present invention to build up a more facile and easier to use process P' for the preparation of a wide variety of end products.

This other object was achieved by a process P' for the preparation of a compound from an aryl aliphatic ketone K, said process P' comprising:
- synthesizing the aryl aliphatic ketone K by the process P as above described, and
- causing the aryl aliphatic ketone K to react in accordance with a single or multiple chemical reaction scheme involving at least one reagent other than the aryl aliphatic ketone K, wherein at least one product of the chemical reaction scheme is the end compound that is not further caused to be chemically converted into another compound.

Aryl aliphatic ketones K obtained by the process P can be seen as easily functionalizable hydrophobic platform molecules incorporating an aryl groupement and a long aliphatic chain. Downstream chemistry of high industrial interest can be realized starting from key intermediate aryl aliphatic ketones K, especially in order to design and develop new valuable compounds, with a particular interest for surfactants.

The chemical reaction scheme can be a single reaction scheme. A single reaction scheme is advantageously represented as follows:

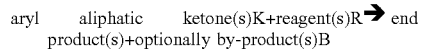
aryl aliphatic ketone(s)K+reagent(s)R→ end product(s)+optionally by-product(s)B Alternatively, the chemical reaction scheme can be a multiple reaction scheme. A multiple reaction scheme is advantageously represented as follows:

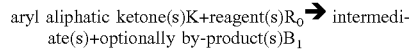
aryl aliphatic ketone(s)K+reagent(s)$R_0$→ intermediate(s)+optionally by-product(s)$B_1$ Optionally N further reaction(s) to convert intermediates into other intermediates:

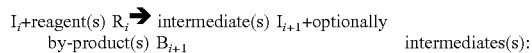
$I_i$+reagent(s) $R_i$→ intermediate(s) $I_{i+1}$+optionally by-product(s) $B_{i+1}$     intermediates(s):

until final intermediate(s) $I_F$ is/are obtained, wherein N is a strictly positive integer that can be equal to 1, 2, 3, 4, 5 or higher, i∈⟦1, N⟧ and $I_{N+1}=I_F$. the final intermediate $I_F$ is then converted to the final end-product:

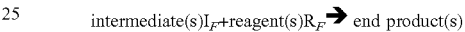
intermediate(s)$I_F$+reagent(s)$R_F$→ end product(s)

Optionally, one or more of the above reactions is conducted in the presence of one or more catalyst(s). Independently of the presence of a catalyst, reagent(s) R of above single reaction scheme and reagent(s) $R_i$ with i∈⟦1, N⟧ of the multiple reaction scheme are, for the purpose of the present invention, considered to react "directly" with the aryl aliphatic ketone K.

In some embodiments, the aryl aliphatic ketone K is caused to react by being subjected to a hydrogenation reaction to obtain a secondary alcohol. The secondary alcohol obtained from the aryl aliphatic ketones K through the reaction with hydrogen may be considered as end product or as an intermediate.

In some other embodiments, the secondary alcohol intermediate is further reacted with a reactant selected from the group consisting of ethylene and/or propylene oxide, sugars, a carboxylic acid, a carboxylic acid derivative and carbon monoxide, thereby giving non-ionic surfactants, branched fatty acids or esters as end products.

The possible intermediate obtained by reacting the secondary alcohol with ethylene and/or propylene oxide can be further reacted with another reagent selected from acrylic acid, acrylate esters, methacrylic acid, methacrylate esters to obtain an end compound that can be serve as a monomer.

Still in other embodiments, the secondary alcohol intermediate is dehydrated to obtain an olefin as new intermediate or as end compound. Preferably, the dehydration is carried out in the substantial absence of an added solvent, preferably in the absence of added solvent, using aluminum oxide, preferably 11-$Al_2O_3$ as catalyst at a temperature in the range of from 250 to 350° C. and for a time of 30 min to 6 h. The dehydration reaction is usually carried out in an inert atmosphere.

In certain embodiments, the aryl aliphatic ketone K is caused to react directly with at least one reagent chosen from the list consisting of sulfonating agents, diesters derived from tartaric acid, phenol and other aromatic mono- or polyalcohols, anilines, formaldehyde, polyols such as glycerol and pentaerythritol, acrylates derivatives, acrylonitrile, and hydroxylamine, thereby obtaining an intermediate or an end compound.

Possible intermediate can further react with another reagent selected from the group consisting of ethylene and/or propylene oxide, sodium hydroxide and hydrogen, thereby obtaining an end compound.

Possible end products obtained by reacting the aryl aliphatic ketone K directly with an aformentioned reagent and then, if needed, with another reagent include anionic surfactants such as dicarboxylate salt derivatives or sulfonates, non-ionic surfactants, polyamines, oximes and ethylenically unsaturated monomers.

In some embodiments, the aryl aliphatic ketone K is caused to react directly, in a single or multiple chemical reaction scheme, with at least one reagent chosen from the list consisting of ammonia, primary or secondary amines and mixtures of at least one aldehyde (including possibly formaldehyde) with ammonia or with at least one primary or secondary amine, thereby obtaining an intermediate or an end compound.

Possible intermediates obtained by reacting aryl aliphatic ketones K directly with the aforementioned reagents include primary, secondary or tertiary aryl alkyl amines, secondary and tertiary aryl alkyl amines themselves substituted by one or two primary, secondary or tertiary amino groups containing substituents, aryl aliphatic ketone monoamines and aryl aliphatic ketone diamines. All these intermediates can also be viewed as end products.

The so-obtained intermediate can further react with a reagent chosen from the group consisting of alkylating agents, acrylate derivatives, hydrogen and hydrogen peroxide, thereby giving end product which can be aryl alkyl quaternary ammonium salt, aryl aliphatic ketone monoquaternary ammonium salt, aryl aliphatic ketone di-quaternary ammonium salt, amphoteric compound such as (poly) aminocarboxylate, aminoxide, aminoxide amine, di-aminoxide, di-aminoxide amine, (di)betaine or (di)sultaine and (di)betaine or (di)sultaine amine compounds (typically with a hydroxyl group). All these end products can also potentially serve as intermediates for forming still other end products.

Detailed Description of the Process P'
1—Making Amines from Aryl Aliphatic Ketones K
1.1) Reductive Amination to Afford Aryl Alkyl Amines The end product can be aryl alkyl amine.

Indeed, at least one aryl aliphatic ketone K (i.e. a single aryl aliphatic ketone or a mixture of aryl aliphatic ketones) that is advantageously synthesized by the process P can be reacted with at least one amine under reductive amination conditions to provide at least one aryl alkyl amine.

An aryl aliphatic ketone K synthesized by the process P is generally a compound of formula (I)

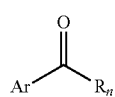

(I)

wherein Ar represents an aryl radical.

Said aryl radical is obtained from removing one hydrogen atom from an aromatic ring which can be optionally substituted by one or more functional group(s).

The term aromatic ring can designate a cyclic conjugated unsaturated hydrocarbon ring having a number of delocalized it electrons following the Huckel rule.

The term aromatic ring encompasses also heteroaromatic ring that is to say cyclic conjugated unsaturated ring containing one or more heteroatoms and having a number of delocalized π electrons following the Huckel rule.

The term aromatic ring encompasses also polycyclic aromatic compounds. In the polycyclic aromatic compounds, the rings can be fused or they can be linked by C—C linkage or by a spiro linkage.

Ar may represent an optionally substituted phenyl group of formula

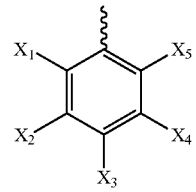

wherein $X_1$, $X_2$, $X_3$, $X_4$ and $X_5$ which can be the same or different represent
  hydrogen or a $C_1$-$C_{24}$ linear or branched hydrocarbon radical having 1 to 24 carbon atoms which can be optionally substituted and/or interrupted by one or more heteroatoms or heteroatom containing groups,
  halogen,
  hydroxy (—OH) or alkoxy group (—OR) wherein R is a linear or branched hydrocarbon radical having 1 to 24 carbon atoms which can be optionally substituted and/or interrupted by one or more heteroatoms or heteroatom containing groups,
  amino group (—NRR') wherein R and R' independently represent a linear or branched hydrocarbon radical having 1 to 24 carbon atoms which can be optionally substituted and/or interrupted by one or more heteroatoms or heteroatom containing groups,
  acyl group (—(C=O)—R) wherein R represent hydrogen or a $C_1$-$C_{24}$ linear or branched hydrocarbon radical having 1 to 24 carbon atoms which can be optionally substituted and/or interrupted by one or more heteroatoms or heteroatom containing groups,
  carboxyl (—COOH) or alkoxycarbonyl group (—(C=O)—OR) wherein R represent a $C_1$-$C_{24}$ linear or branched hydrocarbon radical having 1 to 24 carbon atoms which can be optionally substituted and/or interrupted by one or more heteroatoms or heteroatom containing groups,
  carbamoyl group (—(C=O)—NRR') wherein R and R' independently represent a linear or branched hydrocarbon radical having 1 to 24 carbon atoms which can be optionally substituted and/or interrupted by one or more heteroatoms or heteroatom containing groups,
  alkylsulfonyl group (—$SO_2$—R) or alkylsulfinyl group (—SO—R) or alkylthio (—S—R) wherein R represent a $C_1$-$C_{24}$ linear or branched hydrocarbon radical having 1 to 24 carbon atoms which can be optionally substituted and/or interrupted by one or more heteroatoms or heteroatom containing groups.

Ar may also represent an optionally substituted 2-pyridyl, 3-pyridyl or 4-pyridyl group of formula

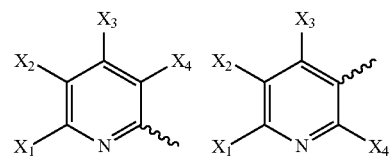

-continued

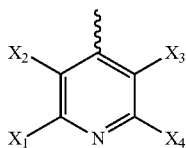

wherein X₁, X₂, X₃ and X₄ which can be the same or different have the same meaning as above described.

Ar may also represent an optionally substituted furan-2-yl or furan-3-yl group of formula

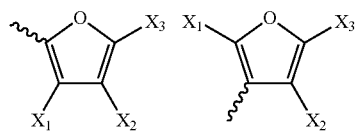

wherein X₁, X₂ and X₃ which can be the same or different have the same meaning as above described.

Ar may also represent an optionally substituted 1H-pyrol-2-yl or 1H-pyrol-3-yl group of formula:

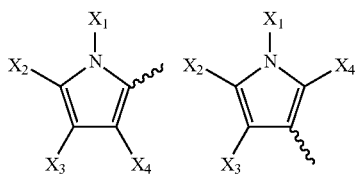

wherein X₁, X₂, X₃ and X₄ which can be the same or different have the same meaning as above described.

Ar may also represent an optionally substituted thiophen-2-yl or thiophen-3-yl group of formula:

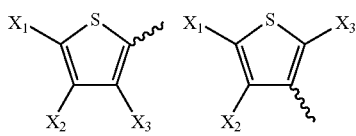

In some embodiments, substituents $X_i$ and $X_{i+1}$ beared by 2 adjacent carbons of the phenyl, the pyridyl, the furanyl, the pyrolyl or the thiophenyl, form together an optionally substituted cyclic moiety said cyclic moiety being an aromatic, heteroaromatic or non-aromatic group.

$R_n$ represents generally a $C_3$-$C_{27}$ aliphatic group, very often a $C_3$-$C_{19}$ aliphatic group, often a aliphatic $C_7$-$C_{17}$ group.

The aliphatic group $R_n$ may be linear or branched.

The aliphatic group $R_n$ may be free of any double bond and of any triple bond. Alternatively, the aliphatic group $R_n$ may comprise at least one —C=C-double bond and/or at least one —CHC— triple bond.

The aliphatic group $R_n$ is advantageously chosen from alkyl groups, alkenyl groups, alkanedienyl groups, alkanetrienyl groups and alkynyl groups.

Preferably, the aliphatic group $R_n$ is chosen from alkyl, alkenyl and alkanetrienyl groups.

More preferably, the aliphatic group $R_n$ is chosen from alkyl and alkenyl groups, generally from $C_3$-$C_{27}$ alkyl and $C_3$-$C_{27}$ alkenyl groups, very often from $C_3$-$C_{19}$ alkyl and $C_3$-$C_{19}$ alkenyl groups and often from $C_7$-$C_{17}$ alkyl and $C_7$-$C_{17}$ alkenyl groups. More preferably, $R_n$ represents an alkyl group, generally a $C_3$-$C_{27}$ alkyl group, very often a $C_3$-$C_{19}$ alkyl group, often a $C_7$-$C_{17}$ alkyl group.

In particular, the at least one aryl aliphatic ketone K of formula (I) can be reacted with at least one amine of formula (II) under reductive amination conditions to afford the at least one aryl alkyl amine of formula (III)

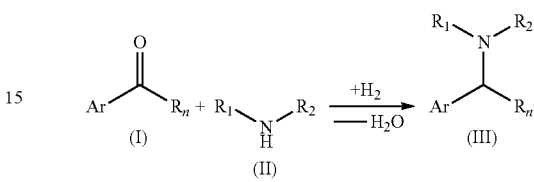

This amination reaction is preferably performed by reacting the ketone (I) and the amine (II) in the presence of a transition metal (e.g. Ni, Co, Cu, Fe, Rh, Ru, Ir, Pd, Pt) based catalyst (typically Pd/C), in a autoclave under hydrogen pressure (typically from 1 atm to 200 bar).

According to a possible embodiment, the reaction is carried out in a solvent. However, the presence of such a solvent is not compulsory and according to a specific embodiment, no solvent is used for this step. The exact nature of the solvent, if any, may be determined by the skilled person. Typical suitable solvents include, without limitation, methanol, ethanol, isopropanol, tert-butanol, THF, 2-methyltetrahydrofuran, 1,4-dioxane, dimethoxyethane, diglyme, water and mixtures thereof.

Besides, this step is usually carried out at a temperature ranging from 15° C. to 400° C. and may be conducted batchwise, semi-continuously or continuously and generally performed either in a batch mode or in a continuous mode using a fixed-bed catalyst (gas-solid or gas-liquid-solid process).

In the above amine formula (II), $R_1$ and $R_2$ independently represent:
- hydrogen or a linear or branched hydrocarbon radical having 1 to 24 carbon atoms which can be optionally substituted and/or interrupted by one or more heteroatoms or heteroatom containing groups (for example $R_1$ and $R_2$ can be selected from H, —CH₃, —CH₂CH₃, propyl, isopropyl, butyl, sec-butyl, isobutyl and tert-butyl),
- ethylamine of formula —CH₂—CH₂—NR'R" wherein R' and R" independently represent hydrogen or a short alkyl group having from 1 to 6 carbon atoms (such as for example CH₃, CH₂CH₃, propyl, isopropyl),
- [poly(ethylenimine)]ethylamine of formula —(—CH₂.CH₂.NH—)ₘ—CH₂—CH₂—NR'R" wherein R' and R" independently represent hydrogen or an alkyl group having from 1 to 6 carbon atoms (such as for example CH₃, CH₂CH₃, propyl, isopropyl) and m is an integer from 1 to 20,
- hydroxyethyl of formula —CH₂—CH₂—OH,
- [poly(ethylenimine)]ethanol of formula —(—CH₂—CH₂—NH—)m-CH₂—CH₂—OH wherein m is an integer from 1 to 20,
- [poly(ethylenoxy)]ethylamine of formula:
—(—CH₂—CH₂—O—)m-CH₂—CH₂—NR'R"
wherein R' and R" independently represent hydrogen or an alkyl group having from 1 to 6 carbon atoms (such as for example CH$_3$, CH$_2$CH$_3$, propyl, isopropyl) and m is an integer from 1 to 100, a N,N-dialkylaminoalkyl radical of formula —(CH$_2$)$_m$—NR'R" wherein m is an integer from 3 to 20 and R' and R" independently represent hydrogen or an alkyl group having 1 to 6 carbon atoms (such as CH$_3$, CH$_2$CH$_3$, propyl, isopropyl), R$_1$ and R$_2$ can also form an alkanediyl radical, typically of formula —(CH$_2$)$_m$— wherein m ranges from 3 to 8, which can be optionally interrupted or substituted by one or more heteroatoms or heteroatom containing groups; in this case, (II) is a cyclic amine such as pyrrolidine, piperidine, morpholine or piperazine.

As examples of amines (II), one can mention: ammonia, dimethylamine, monoethanolamine, diethanolamine, ethylenediamine (EN), diethylenetriamine (DETA), triethylenetetramine (TETA), tetraethylenepentamine (TEPA), aminoethylethanolamine (AEEA), dimethylaminopropylamine (DMAPA) and 3,3'-Iminobis(N,N-dimethylpropylamine).

1.2) Mannich Reaction Involving Condensation with an Aldehyde and an Amine to Afford Aryl Alkyl Amine Compounds The end product can be a ketone amine compound where the carbonyl-adjacent non-aromatic carbon atom is substituted by at least one amine-containing group.

The at least one aryl aliphatic ketone K (i.e. a single aryl aliphatic ketone or a mixture of aryl aliphatic ketones) that is advantageously synthesized by the process P can be reacted with at least one aldehyde and at least one amine under Mannich reaction conditions to provide at least one ketone having its carbonyl-adjacent non-aromatic carbon atom substituted by an amine-containing group and/or by two amine-containing groups.

In particular, aryl aliphatic ketones K of formula (I)

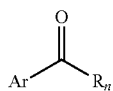

(I)

as above defined, wherein a methylene group is adjacent to the carbonyl group can be represented by formula (I')

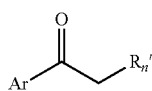

(I')

wherein R$_n$' represents an aliphatic group, generally a C$_2$-C$_{26}$ aliphatic group, very often a C$_2$-C$_{18}$ group, often a C$_6$-C$_{16}$ group.

The at least one aryl aliphatic ketone K of formula (I') can be reacted with at least one aldehyde of formula (IV) and at least one amine of formula (II) under Mannich reaction conditions to afford at least one ketone (Va) having its carbonyl-adjacent non-aromatic carbon atom substituted by an amine-containing group and/or at least one ketone (Vb) having its carbonyl-adjacent non-aromatic carbon atom substituted by two amine-containing groups.

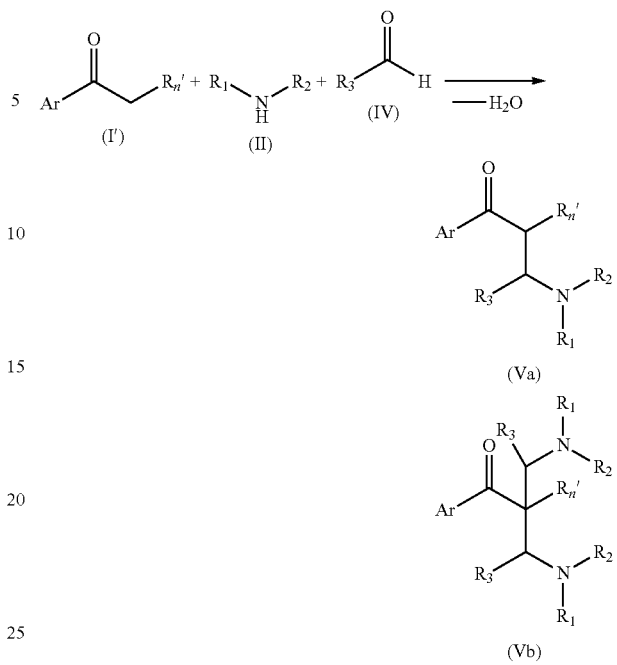

In the amine of formula (II), R$_1$ and R$_2$ are as previously defined in part 1.1.

Regarding the aldehyde (IV), R$_3$ can represent:

hydrogen or a linear or branched hydrocarbon radical having from 1 to 24 carbon atoms which can be optionally substituted and/or interrupted by one or more heteroatoms or heteroatom containing groups (for example, R$_3$ can be selected from —H, —CH$_3$, —CH$_2$CH$_3$, propyl, isopropyl, butyl, sec-butyl, isobutyl and tert-butyl), or An aryl radical which is obtained from removing one hydrogen atom from an aromatic ring which can be optionally substituted by one or more functional group(s).

The term aromatic ring can designate a cyclic conjugated unsaturated hydrocarbon ring having a number of delocalized π electrons following the Huckel rule.

The term aromatic ring encompasses also heteroaromatic ring that is to say cyclic conjugated unsaturated ring containing one or more heteroatoms and having a number of delocalized π electrons following the Huckel rule. The term aromatic ring encompasses also polycyclic aromatic compounds.

In the polycyclic aromatic compounds, the rings can be fused or they can be linked by C—C linkage or by a spiro linkage.

For example, R$_3$ can be phenyl, fur-2-yl, fur-3-yl, para-hydroxyphenyl, para-methoxyphenyl or 4-hydroxy-3-methoxyphenyl.

As examples of aldehydes (IV), one can mention formaldehyde, ethanal, propanal, butanal, furfural, hydroxymethylfurfural, vanillin and para-hydroxybenzaldehyde.

The Mannich reaction can be conducted under acidic conditions when the amine (II) is in its protonated form, for example as a hydrochloride salt form.

The reaction is usually carried out by contacting the ketone (I'), the aldehyde (IV) and the amine (II) (or its protonated salt which can be generated in-situ by adding a stoichiometric amount of acid), optionally in the presence of an added solvent in a reaction zone at a temperature from 15° C. to 300° C. As examples of suitable solvents to conduct the reaction, one can mention: methanol, ethanol, isopropanol, toluene, xylenes, diglyme, dioxane, THF, methyl-THF, DMSO, water and mixtures thereof etc.

The amine (II) or its protonated salt as well as the aldehyde (IV) can be used in molar excess and the excess reactants can be recovered at the end of the reaction and recycled.

The reaction can also be catalyzed by the addition of a suitable Bronsted or a Lewis acid. One can mention for example: $H_2SO_4$, HCl, triflic acid, p-toluenesulfonic acid, perchloric acid, $AlCl_3$, $BF_3$, metal triflate compounds such as aluminium triflate, bismuth triflate, heterogeneous solid acids such as Amberlyst resins, zeolithes, etc.

The water generated during the reaction can be optionally trapped thanks to a Dean-Stark apparatus.

If the reaction is conducted under acidic conditions, after subsequent work-up, the products (Va) and/or (Vb) are obtained in the form of their protonated salts which can be neutralized in a second stage by the reaction with an aqueous solution of a suitable base for example: NaOH, KOH, $NH_4OH$ or $Na_2CO_3$.

The desired ketone amines (Va) and/or (Vb) are obtained after appropriate work-up. The skilled person is aware of representative techniques so that no further details need to be given here.

2—Making Quaternary Ammoniums from Aryl Aliphatic Ketones K 2.1) Quaternization of Aryl Alkyl Amine (III) to Afford Aryl Alkyl Quaternary Ammonium Compounds The end product can be an aryl alkyl quaternary ammonium compound.

Such an aryl alkyl quaternary ammonium compound can be obtained as end product when at least one aryl alkyl amine obtained from the at least one aryl aliphatic ketone K according to the reaction described in part 1.1 is a tertiary amine. For example, when the aryl alkyl amine is of formula (III), this happens when $R_1$ and $R_2$ differ from a hydrogen atom.

Accordingly, at least one aryl alkyl tertiary amine obtained from at least one aryl aliphatic ketone K according to the reaction described in part 1.1 can be reacted with at least one alkylating agent to obtain at least one aryl alkyl quaternary ammonium salt.

In particular, at least one tertiary amine (III) obtained from the at least one aryl aliphatic ketone K of formula (I) according to part 1.1 can be reacted with at least one alkylating agent (VI) of formula $R_4$—X to obtain at least one aryl alkyl quaternary ammonium salt (VII), as schemed below:

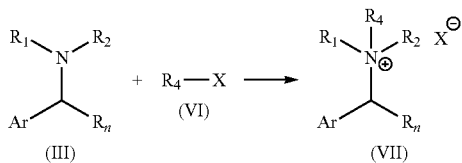

As already pointed out, amines (III) useful for use in present part 2.1 are tertiary amines. Advantageously, the tertiary amines (III) useful for use in present part 2.1 are tertiary amines wherein $R_1$ and $R_2$ independently represent a linear or branched hydrocarbon radical having from 1 to 24 carbon atoms which can be optionally substituted and/or interrupted by one or more heteroatoms or heteroatom containing groups (for example $R_1$ and $R_2$ can be selected from —$CH_3$, —$CH_2CH_3$, propyl, isopropyl, butyl, sec-butyl, isobutyl and tert-butyl) and tertiary amines wherein $R_1$ and $R_2$ form an alkanediyl radical, typically of formula —$(CH_2)m$- wherein m ranges from 3 to 8, which can be optionally interrupted and/or substituted by one or more heteroatoms or heteroatom containing groups.

The group X contained in the alkylating agent (VI) and that constitutes the counter anion of the salt (VII) is a leaving group, typically a halide such as Cl, Br or I, methylsulfate (—$SO_4Me$), sulfate (—$SO_4$), a sulfonate derivative such as methanesulfonate (—$O_3S$—$CH_3$), para-toluenesulfonate (—$O_3S$—$C_7H_7$) or trifluoromethanesulfonate (—$O_3S$—$CF_3$).

In reactant (VI), $R_4$ represents a linear or branched hydrocarbon radical having 1 to 10 carbon atoms which can be optionally substituted and/or interrupted by a substituted or unsubstituted aromatic group and/or a heteroatom or heteroatom containing group. For example, $R_4$ can be: —$CH_3$, —$CH_2CH_3$, benzyl, furfuryl.

As examples of alkylating agent (VI), one can mention dimethyl sulfate, methyl chloride, methyl bromide, methyl triflate, benzyl chloride and epichlorhydrin.

This reaction can be carried out by contacting both reactants in a reaction zone at a temperature from 15° C. to 400° C., optionally in the presence of an added solvent such as methanol, ethanol, isopropanol, toluene, a xylene, diglyme, dioxane, THF, methyl-THF or DMSO. The alkylating agent can be used in stoichiometric amounts or in excess and the excess reactant can be recovered after the reaction following a suitable work-up and recycled. The skilled person is aware of representative work-up techniques so that no further details need to be given here.

2.2) Quaternization Reaction of Tertiary Amine Compounds to Afford Quaternary Ammonium Salt Compounds The end compound can be a aryl aliphatic ketone (di) quaternary ammonium salt.

Such a quaternary ammonium salt can be obtained as end product when at least one ketone amine compound obtained from at least one aryl aliphatic ketone K according to the reaction described in part 1.2 is a tertiary amine. For example, when the amine compound is of formula (Va) or (Vb), this happens when $R_1$ and $R_2$ differ from a hydrogen atom.

At least one ketone tertiary amine obtained from at least one aryl aliphatic ketone K according to the reaction described in part 1.2 can be reacted with at least one alkylating agent to obtain at least one ketone quaternary ammonium salt.

For example, at least one ketone amine (Va) and/or at least one ketone amine (Vb) obtained from the at least one aryl aliphatic ketone K of formula (I) according to part 1.2 can be reacted with at least one alkylating agent (VI) of formula $R_4$—X to obtain respectively at least one ketone quaternary ammonium salt (VIIIa) and/or at least one quaternary ammonium salt (VIIIb), as schemed below:

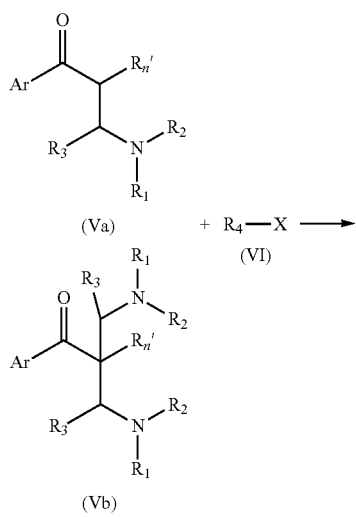

(Va)  + R₄—X ⟶ (VI)

(Vb)

Certain amines of formula (III) that are suitable for undergoing this reaction comply with formula (III')

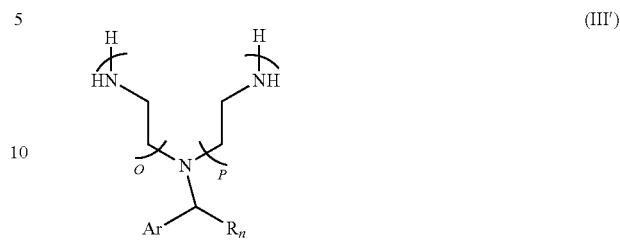

(III')

wherein $R_n$ has the same meaning as in formula (I) and wherein o and p are integers from 0 to 20, preferably from 2 to 20, possibly from 4 to 20.

In particular, at least aryl alkyl amine of formula (III') can be reacted with at least one alkylating agent (IX) to afford at least one amphoteric compound (X), as schemed hereinafter:

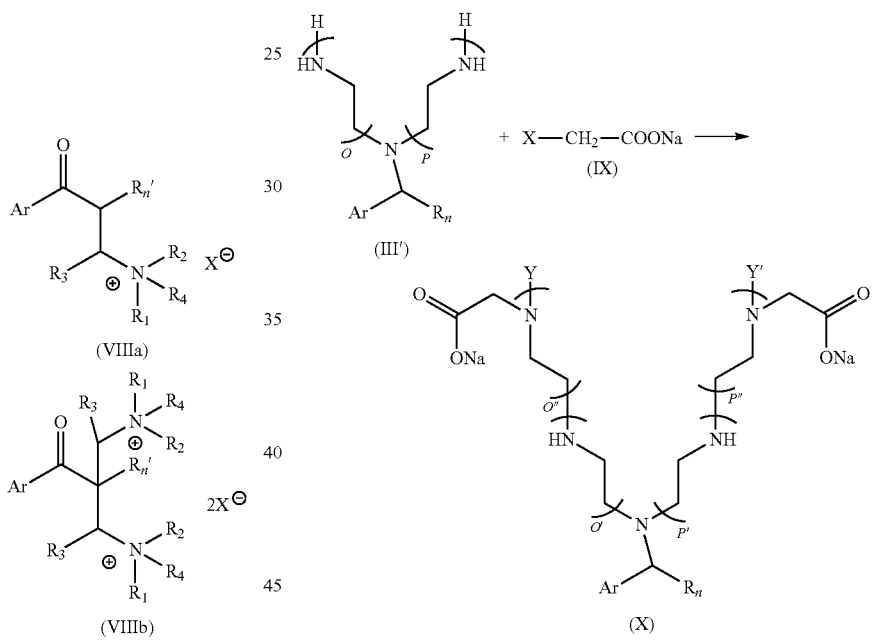

(VIIIa)

(VIIIb)

The substituents $R_1$, $R_2$, $R_4$ and the group X meet the same definitions as the ones provided in part 2.1 while the substituent $R_3$ has the same definition as in part 1.2.

This reaction can be carried out as indicated in part 2.1.

3—Making Amphoterics from Aryl Aliphatic Ketones K

The End Compound can be a Twin-Tail (Poly)Aminocarboxylate.

3.1) Synthesis of Twin-Tail (Poly)Aminocarboxylates

At least one aryl alkyl amine prepared from at least one aryl aliphatic ketone K according to part 1.1 can be reacted with at least one alkylating agent to afford at least one amphoteric compound, notably when said aryl alkyl amine is itself substituted by at least one, possibly by two and only two, primary and/or secondary amino group containing substituents.

The reaction is usually conducted by contacting both reactants in a reaction zone at temperature from 15° C. to 400° C. and optionally in the presence of an added solvent. As examples of suitable solvents, one can mention methanol, ethanol, isopropanol, DMSO, acetonitrile, water, THF, dioxane and mixtures thereof.

In a preferred embodiment, the pH of the reaction mixture is maintained during the course of the reaction from 8.5 to 9.5. This adjustment can be done by adding required amounts of concentrated NaOH and/or HCl aqueous solutions to the reaction medium.

Importantly, by adjusting the stoichiometry of the reaction (molar excess of (IX) with respect to (III')), it is possible to adjust the average degree of alkylation of the starting amine (III') which means the average number of methylenecarboxylate groups (—CH₂—CO₂Na) contained in (X).

In the product (X), o', o", p' and p" are integers ranging from 0 to 20 provided that at least one of o" and p" is of at least 1. Preferably, o', o", p' and p" are integers ranging from 1 to 20, possibly from 2 to 20, and the following equalities must be respected:

$$o'+o''=o \text{ and } p'+p''=p.$$

The substituents Y and Y' can be independently a hydrogen atom or a methylenecarboxylate fragment (—CH$_2$—CO$_2$Na).

It has to be understood that the values of o', o", p' and p" reflect the degree of alkylation and that mixture of compounds (X) with different values for o', o", p' and p" and with different substituents Y and Y' can be obtained. Globally, one can say that when the molar amount of the alkylating agent (IX) is increased, the value of o" and p" increase (and consequently o' and p' decrease).

The group X contained in the alkylating agent (IX) is a leaving group, and has the same meaning as in part 2.1.

As an example, one can consider the reaction between the ethylenediamine-derived amine of type (III') and 2 equivalents of sodium monochloroacetate ((IX) with X=Cl). In this case, the following mixture can be obtained:

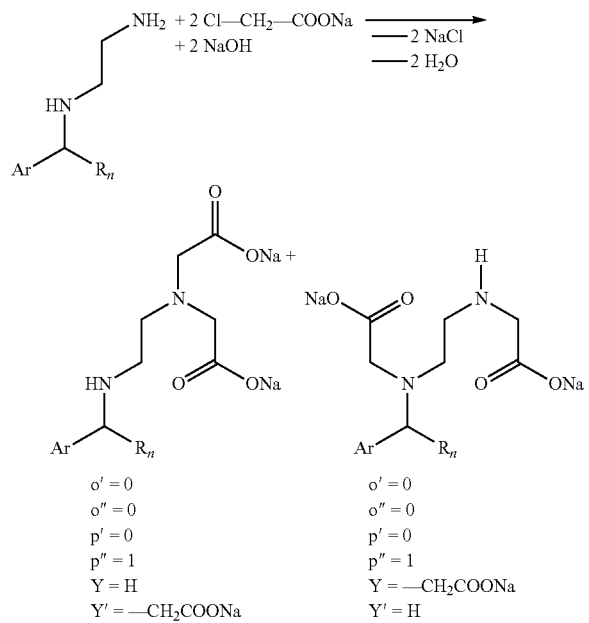

3.2) Second Synthesis of (Poly)Aminocarboxylates

At least one aryl alkyl amine prepared from at least one aryl aliphatic ketone K according to part 1.1 can be reacted with at least one acrylate derivative (especially a hydrocarbyl acrylate of formula CH$_2$=CH—CO$_2$A wherein A is hydrocarbyl, preferably C$_1$-C$_7$ hydrocarbyl, more preferably C$_1$-C$_4$ alkyl), to afford at least one amphoteric compound, notably when said aryl alkyl amine is itself substituted by at least one, possibly by two and only two, primary and/or secondary amino group containing substituents.

Certain amines of formula (III) that are suitable for undergoing this reaction comply with formula (III') as described in part 3.1.

In particular, the at least one aryl alkyl amine (III') obtained from the at least one aryl aliphatic ketone K (I) according to part 1.1, wherein R$_n$ has the same meaning as in formula (III) and wherein o and p are integers from 0 to 20, preferably from 2 to 20, possibly from 4 to 20, is reacted in a first step with at least one acrylate derivative, such as the above described hydrocarbyl acrylate, to undergo conjugate additions affording at least one (poly)ester, such as the hydrocarbyl (poly)ester of the formula (XIa')—not represented—obtained by generalizing/replacing methyl (Me) by hydrocarbyl (A substituent) in below formula (XIa). The at least one obtained ester (XIa') is then saponified in a second stage using an aqueous NaOH solution to afford at least one amphoteric compound, such as the amphoteric compound of formula (XIb)

The following reaction scheme corresponds to the case when the acrylate derivative is CH$_2$=CH—CO$_2$Me (A is methyl Me):

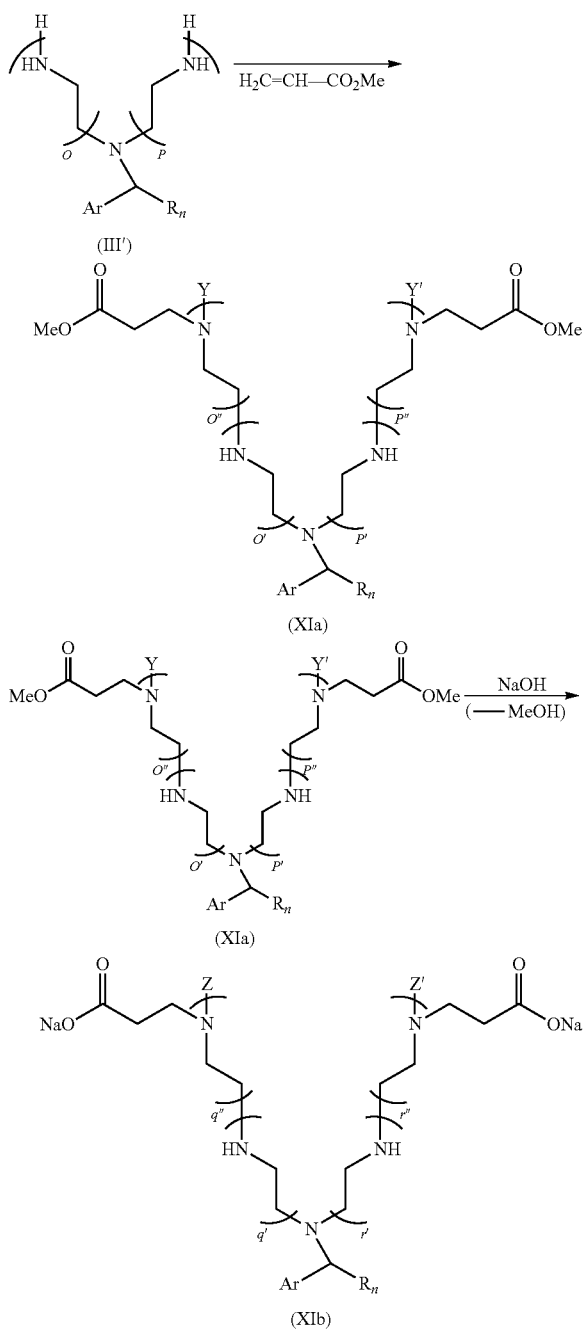

Typically, in the intermediate (XIa') [e.g. (XIa)], the substituents Y and Y' represent independently either a hydrogen atom or a hydrocarbyl ethylenecarboxylate fragment (—CH$_2$—CH$_2$—CO$_2$A), in particular a methyl ethylenecarboxylate fragment (—CH$_2$—CH$_2$—CO$_2$Me).

In the final amphoteric derivative (XIb), the substituents Z and Z' independently represent a hydrogen atom or an ethylenecarboxylate fragment (—CH$_2$—CH$_2$—CO$_2$Na).

o', o", p' and p" in the intermediate (XIa') [e.g. (XIa)], and q', q", r' and r" in the final product (XIb) are integers ranging from 0 to 20 provided that at least one of o" and p" is of at least 1 and at least one of q" and r" is of at least 1.

Preferably, o', o", p' and p" in the intermediate (XIa') [e.g. (XIa)], and q', q", r' and r" in the final product (XIb) are integers ranging from 1 to 20, possibly from 2 to 20.

In addition, the following equalities must be respected:

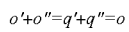

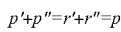

The first step of the reaction is carried out by contacting both reactants in a reaction zone at temperature from 15° C. to 400° C. The whole amount of the reactants can be introduced directly in the reaction mixture, but in a preferred embodiment the acrylate derivative is progressively added into the reaction mixture in order to limit polymerization side reactions. The reaction can be optionally conducted in the presence of an added solvent, for example: methanol, ethanol, isopropanol, THF, dioxane, ethyl acetate, acetonitrile, etc.

The acrylate derivative can be used in excess with respect of the amine (III').

The intermediate ester (XIa') [e.g. methyl ester (XIa)] is advantageously isolated after removal of excess of acrylate derivative and optional solvents using standard techniques well known by the skilled person of the art. The second step is then carried out by contacting intermediate (XIa') with an appropriate amount of an aqueous solution of NaOH (the molar amount of NaOH is equal or higher than the molar amount of ester fragments that need to be saponified), optionally in the presence of an added solvent, such as methanol, ethanol, isopropanol, acetonitrile, DMSO, water, THF or mixture thereof, and at a temperature from 15° C. to 400° C.

During the first step, the acrylate derivative can be used in a molar excess, and generally the stoichiometric ratio between amine (III') and acrylate will dictate the average degree of alkylation of the starting amine (III'), meaning the average number of hydrocarbyl ethylenecarboxylate (—CH$_2$—CH$_2$—CO$_2$A) fragments contained in the intermediate (XIa') or the like and consequently the average number of ethylenecarboxylate (—CH$_2$—CH$_2$—CO$_2$Na) fragments contained in the final amphoteric product (XIb).

It has to be understood that when the molar excess of acrylate derivative is increased during the first step, the average number of hydrocarbyl ethylenecarboxylate (—CH$_2$—CH$_2$—CO$_2$A) fragments contained in the intermediate (XIa') and the average number of ethylenecarboxylate (—CH$_2$—CH$_2$—CO$_2$Na) fragments contained in the final amphoteric product (XIb) are increased.

Usually, a mixture of intermediates (XIa') [e.g. (XIa)] with different values for o', o", p', p" and different substituents Y and Y' is obtained at the end of the first step.

Same applies for the final products (XIb) where mixtures of derivatives with different values for q', q", r', r" and different substituents Z and Z' are obtained at the end of the second step.

As an example, one can consider the reaction between the ethylenediamine-derived amine of type (III') and 2.5 equivalents of methyl acrylate followed by saponification.

In this case the following mixture can be obtained:

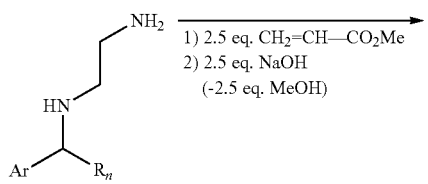

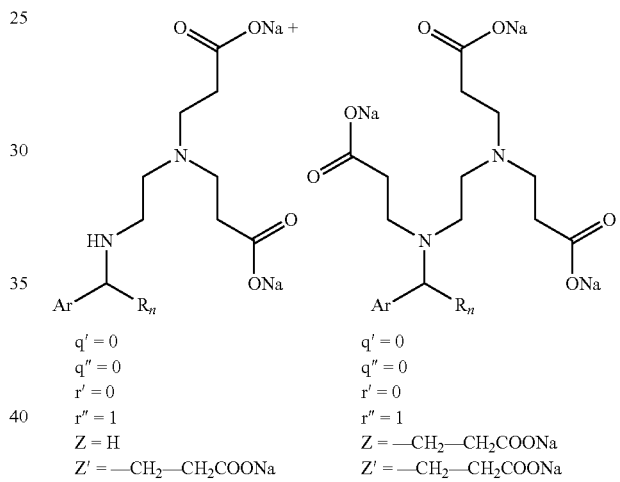

3.3) Third Synthesis of (Poly)Aminocarboxylates

The reaction is conducted as described in part 3.1, except that the at least one starting amine (III) made from the at least one aryl aliphatic ketone K (I) is an amine (III") which contains one or two terminal 2-hydroxyethyl fragment(s) (—CH$_2$—CH$_2$—OH) based on the nature of Y.

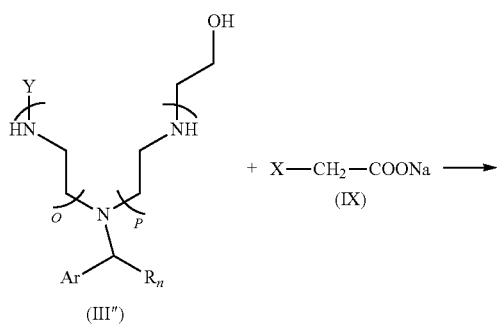

-continued

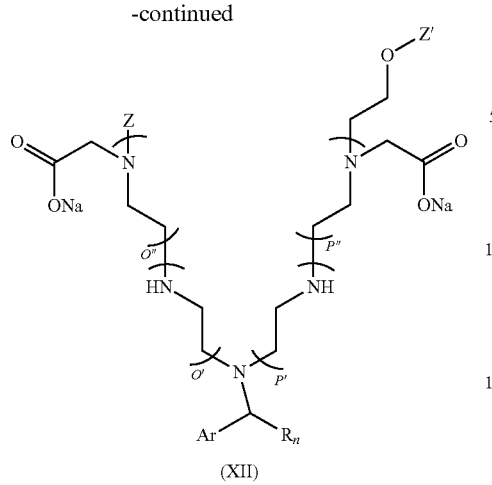

(XII)

Z = -H or -CH$_2$CO$_2$Na if Y = -H
Z = -CH$_2$CH$_2$OH or —CH$_2$CH$_2$—O—CH$_2$CO$_2$Na if
Y = -CH$_2$CH$_2$OH

What has been said in part 3.1 regarding the degree of alkylation applies in this case as well.

In the reaction scheme above:

o and p in the reactant (III″) are integers from 0 to 20, preferably from 2 to 20, possibly from 4 to 20;

o′, o″, p′ and p″ in the product (XII) are integers ranging from 0 to 20, preferably, o′, o″, p′ and p″ in the product (XII) are integers ranging from 1 to 20, possibly from 2 to 20, and the following equalities must be respected:

$$o'+o''=o$$

$$p'+p''=p.$$

The substituent Y in the reactant (III″) represents a hydrogen atom or a 2-hydroxyethyl fragment (—CH$_2$—CH$_2$—OH).

The substituent Z contained in the product (XII) represents:

hydrogen or methylenecarboxylate (—CH$_2$—CO$_2$Na) when Y is hydrogen, 2-hydroxyethyl (—CH$_2$—CH$_2$—OH) or the ether fragment —CH$_2$—CH$_2$—O—CH$_2$—CO$_2$Na when Y is 2-hydroxyethyl fragment (—CH$_2$—CH$_2$—OH).

The substituent Z′ represents hydrogen or methylenecarboxylate fragment —CH$_2$—CO$_2$Na.

As described in part 3.1, a mixture of products (XII) containing different numbers of methylenecarboxylate fragments (—CH$_2$—CO$_2$Na), which means different values for o′, o″, p′ and p″ and different substituents Z and Z′, can be obtained.

As an example, one can consider the reaction between the aminoethylethanolamine-derived amine of type (III″) and 1.5 equivalents of sodium monochloroacetate [(IX) with X=Cl]. In this case, the following mixture can be obtained:

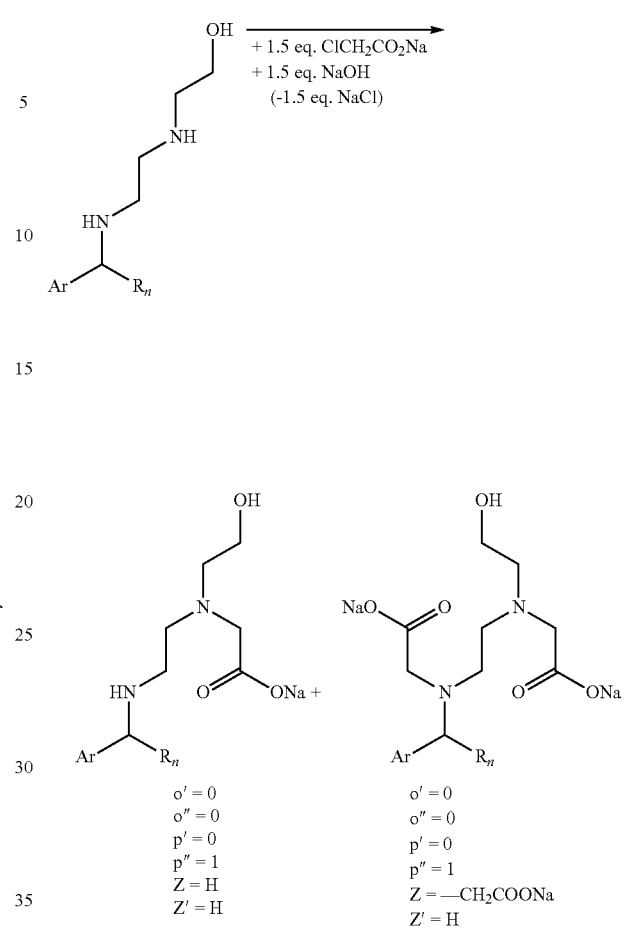

o′ = 0
o″ = 0
p′ = 0
p″ = 1
Z = H
Z′ = H o′ = 0
o″ = 0
p′ = 0
p″ = 1
Z = —CH$_2$COONa
Z′ = H 3.4) Fourth Synthesis of (Poly)Aminocarboxylates The reaction is conducted as described in part 3.2, except that the at least one starting amine (III) made from the at least one aryl aliphatic ketone K (I) is an amine (III″) which contains one or two terminal 2-hydroxyethyl fragment(s) (—CH$_2$—CH$_2$—OH) based on the nature of Y.

An exemplary reaction scheme is:

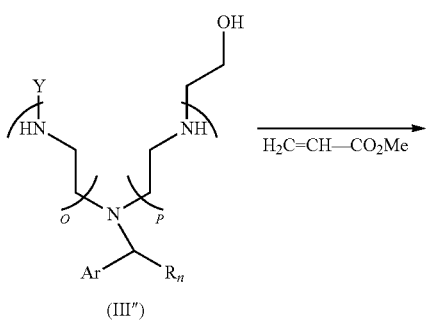

(III″)

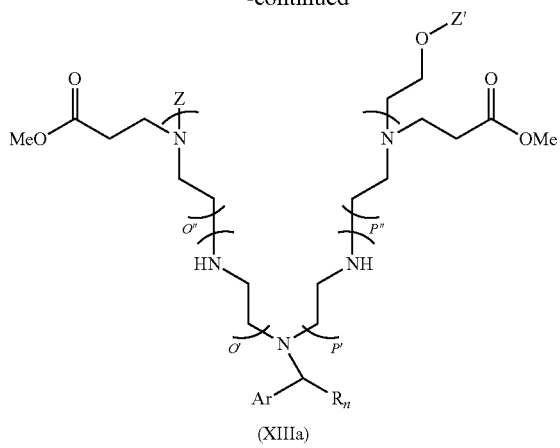

(XIIIa)

Z = —H or —CH₂CH₂CO₂Me if Y = —H
Z = —CH₂CH₂OH or —CH₂CH₂—O—CH₂CH₂CO₂Me if Y = —CH₂CH₂OH
Z' = H or —CH₂CH₂CO₂Me

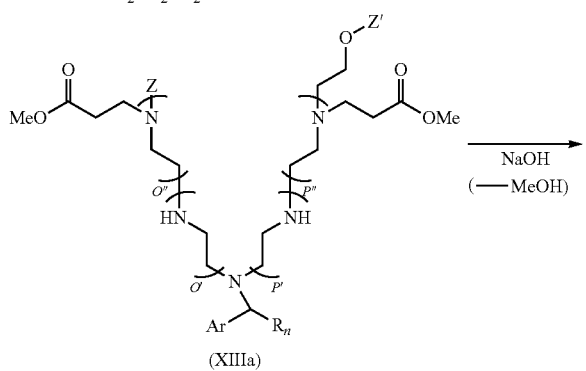

(XIIIa)

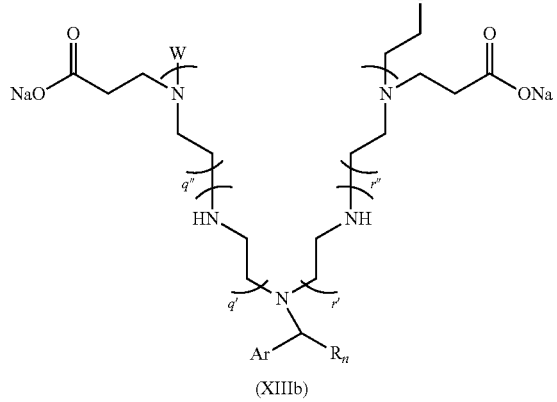

(XIIIb)

W = —H or —CH₂CH₂CO₂Na if Y = —H
Z = —CH₂CH₂OH or —CH₂CH₂—O—CH₂CH₂CO₂Na if Y = —CH₂CH₂OH
W' = H or —CH₂CH₂CO₂Na

As in part 3.2, this exemplary reaction scheme can be generalized by replacing $CH_2{=}CH{-}CO_2Me$ acrylate by hydrocarbyl acrylate of formula $CH_2{=}CH{-}CO_2A$, wherein A is as defined in part 3.2, and more generally by whatever acrylate derivative.

The substituent Y in the reactant (III″) represents a hydrogen atom or a 2-hydroxyethyl fragment (—CH₂—CH₂—OH).

In the above reaction scheme:
o and p in the reactant (III″) are integers from 0 to 20, preferably from 2 to 20, possibly from 4 to 20;
o', o″, p' and p″ in the intermediate (XIIIa) [or in its non-represented generalization (XIIIa') wherein Me is replaced by substituent A] and q', q″, r' and r″ in the final product (XIIIb) are integers ranging from 0 to 20 provided that at least one of o″ and p″ is of at least 1 and at least one of q″ and r″ is of at least 1.

Preferably, o', o″, p' and p″ in the intermediate (XIIIa) or (XIIIa'), and q', q″, r' and r″ in the final product (XIIIb) are integers ranging from 0 to 20, possibly from 2 to 20.

In addition, the following equalities must be respected:

$$o'+o''=q'+q''=o$$

and $$p'+p''=r'+r''=p$$

The substituent Z in the intermediate (XIIIa') represents:
hydrogen or hydrocarbyl ethylenecarboxylate (—CH₂—CH₂—CO₂A) when Y is hydrogen,
2-hydroxyethyl fragment (—CH₂—CH₂—OH) or the ether fragment —CH₂—CH₂—O—CH₂—CH₂—CO₂A when Y is —CH₂CH₂OH.

The substituent Z' in the intermediate (XIIIa') represents either hydrogen or hydrocarbyl ethylenecarboxylate (—CH₂—CH₂—CO₂A). Thus, for example, when (XIIIa') is (XIIIa), Z' represents either hydrogen or methyl ethylenecarboxylate (—CH₂—CH₂—CO₂Me)

The substituent W in the end compound (XIIIb) represents:
hydrogen or ethylenecarboxylate (—CH₂—CH₂—CO₂Na) if Y is hydrogen
2-hydroxyethyl fragment (—CH₂—CH₂—OH), or the ether fragment —CH₂—CH₂—O—CH₂—CH₂—CO₂Na if Y is —CH₂CH₂OH,
while the substituent W' in the end compound (XIIIb) represents either hydrogen or ethylenecarboxylate (—CH₂—CH₂—CO₂Na).

What has been said in part 3.2 regarding the impact on the alkylation degree of the molar ratio between the acrylate derivative and the substrate (III″) used in the first reaction step applies here as well.

As described in part 3.2, a mixture of intermediates (XIIIa') [e.g. (XIIIa)] and a mixture of end products (XIIIb) are usually obtained.

4—Aminoxides 4.1) Synthesis of Aminoxide Amines

The end compound can be an aminoxide amine, that is to say an amine substituted by at least one aminoxide group containing substituent. The aminoxide amine can be substituted by one and only one or two and only two aminoxide group containing substituent(s)

At least one aminoxide amine can be obtained from at least one tert-amino amine (that is to say an amine that is itself substituted by at least one tert-amino group containing substituent), which is itself previously obtained from at least one aryl aliphatic ketone K.

To this effect, a certain twin-tail amine of formula (III) obtained from at least one aryl aliphatic ketone K of formula (I) is advantageously used as reagent, namely a twin-tail tert-amino amine of formula (III‴):

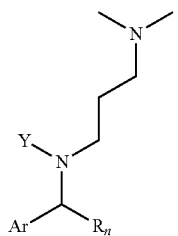

(III'''')

The following reaction scheme can be followed:

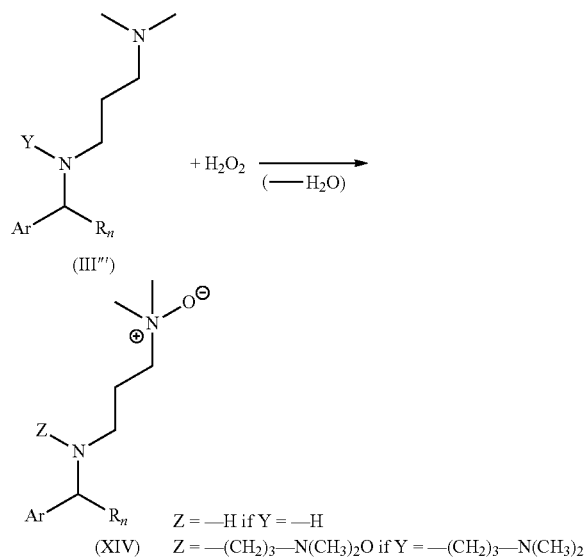

In the above scheme, Y is either hydrogen or 3-dimethylaminopropyl fragment (—CH$_2$—CH$_2$—CH$_2$—N(CH$_3$)$_2$); Z is hydrogen when Y is hydrogen and Z is the 3-dimethylaminoxide propyl fragment (—CH$_2$—CH$_2$—CH$_2$—N(CH$_3$)$_2$O) when Y is 3-dimethylaminopropyl fragment (—CH$_2$CH$_2$CH$_2$—N(CH$_3$)$_2$).

This reaction can be conducted by contacting the twin-tail tert-amino amine (III''') obtained from the aryl aliphatic ketone K (I) with H$_2$O$_2$ (which can be used dissolved in aqueous solution) in a reaction zone at a temperature ranging from 15° C. to 400° C. and optionally in the presence of an added solvent. As examples of suitable solvents, one can mention methanol, ethanol, isopropanol, DMSO, acetonitrile, water, THF, dioxane or a mixture thereof.

In a preferred embodiment, H$_2$O$_2$ solution is progressively added into the reaction medium and can be used in molar excess with respect of the twin-tail tert-amino amine (III'''). The excess of H$_2$O$_2$ can be decomposed at the end of the reaction using appropriate techniques well known by the skilled person of the art.

4.2) Synthesis of Aminoxide Derivative

In particular, at least one aminoxide compound of formula (XVIb) can be obtained from at least one aryl aliphatic ketone K of formula (I) using the ketone amine of formula (Vb) as intermediates.

It goes without saying that at least one aminoxide derivative of formula (XVIa) can likewise be obtained from at least one aryl aliphatic ketone K of formula (I) using the ketone amine of formula (Va) as intermediate.

A suitable reaction scheme is described hereinafter:

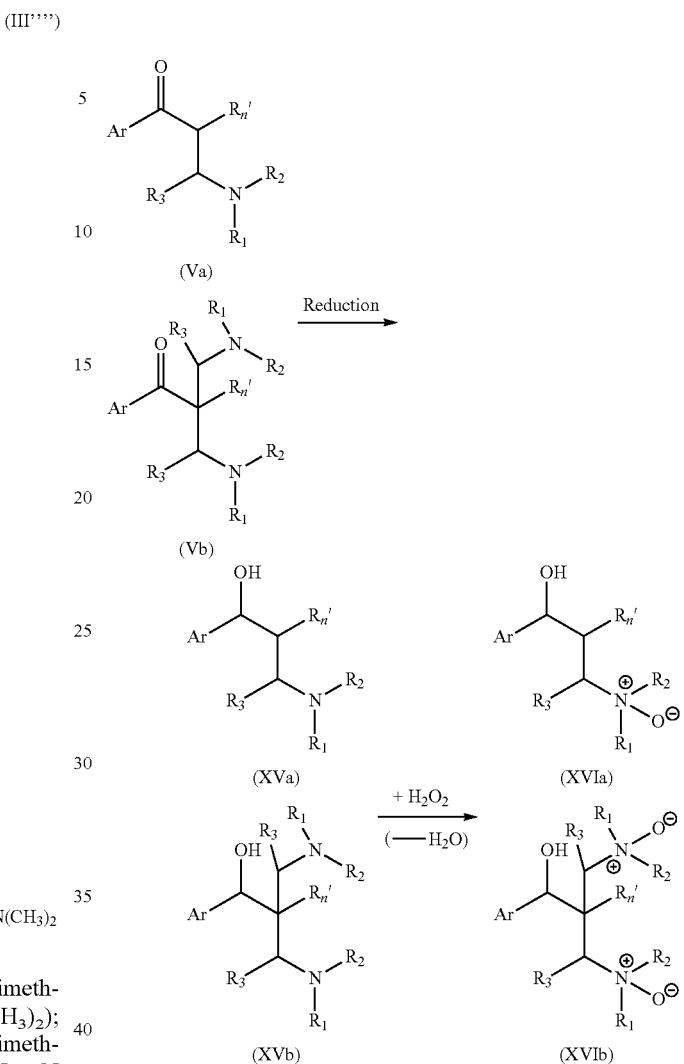

In a first step, the ketone (Va) or (Vb) or a mixture thereof is reduced respectively to the alcohol derivative (XVa) or (XVb) or a mixture thereof.

As example of suitable reductants that can be used for this first step, one can mention H$_2$. In this case, the reaction must be conducted in the presence of a suitable transition metal (e.g. Fe, Ru, Co, Rh, Ir, Ni, Pd, Pt, Cu) based catalyst (for example Pd/C). The reaction can be carried out under a hydrogen pressure (typically from 1 atm to 200 bar) and at temperature ranging from 15° C. to 400° C. Optionally, the reaction is conducted in the presence of an added solvent such as methanol, ethanol, isopropanol, tert-butanol, dioxane, dimethoxyethane, diglyme or a mixture thereof.

Another example of a suitable reductant for this first step is a secondary alcohol, preferably isopropanol which acts as a sacrificial reagent. In this case, the reaction requires the need of a metal based (e.g. Ni, Al, In, Ru, Zr) catalyst (e.g. Al(OiPr)$_3$) and acetone is formed as by-product. Importantly acetone can be removed during the reaction thanks to distillation in order to displace equilibrium toward the formation of (XVa) and (XVb).

The second step consists in the oxidation using H$_2$O$_2$ of the tertiary amine group of the compound of formula (XVa) and/or the compound of formula (XVb) to form respectively the aminoxide derivative of formula (XVIa) and/or the aminoxide compound of formula (XVIb).

This second step can be carried out as described in part 4.1.

$R_1$, $R_2$ and $R_3$ have the same definitions as in part 2.2.

5—Making Betaines and Sultaines from Aryl Aliphatic Ketones K 5.1) Synthesis of (Di)Betaine and (Di)Sultaine The end compound can be a (di)betaine amine, that is to say an amine substituted by at least one betaine group containing substituent. The (di)betaine amine can be an amine substituted by one and only one or two and only two betaine group containing substituent(s).

The end compound can be a (di)sultaine amine, that is to say an amine substituted by at least one sultaine group containing substituent. The (di)sultaine amine can be an amine substituted by one and only one or two and only two sultaine group containing substituent(s).

At least one (di)betaine amine can be obtained from at least one tert-amino amine (that is to say an amine that is itself substituted by at least one tert-amino group containing substituent), which is itself previously obtained from at least one aryl aliphatic ketone K.

At least one (di)sultaine amine can be obtained from at least one tert-amino amine (that is to say an amine that is itself substituted by at least one tert-amino group containing substituent), which is itself previously obtained from at least one aryl aliphatic ketone K.

To obtain at least one (di)betaine amine a certain aryl alkyl amine of formula (III) obtained from at least one aryl aliphatic ketone K advantageously synthesized by the process P, is used as a reagent, namely a twin-tail tert-amino amine of formula (III''').

Said tert-amino amine (III''') is reacted with a compound of formula:

X-Alk-$R_0$ wherein:
X is a leaving group,
Alk is an alkylene group, and
$R_0$ is —$CO_2M$ with M being an alkaline metal.
Methylene is preferred as the alkylene group Alk.
Na is preferred as the alkaline metal M.

The leaving group X is typically a halide such as Cl, Br or I, methylsulfate (—$SO_4Me$), sulfate (—$SO_4$—), a sulfonate derivative such as methanesulfonate (—$O_3S$—$CH_3$), para-toluenesulfonate (—$O_3S$—$C_7H_7$) or trifluoromethanesulfonate (—$O_3S$—$CF_3$).

To obtain at least one (di)sultaine amine, the same certain aryl alkyl amine of formula (III) obtained from at least one aryl aliphatic ketone K advantageously synthesized by the process P, namely a twin-tail tert-amino amine of formula (III'''), is used as a reagent.

Said tert-amino amine (III''') is reacted with a compound of formula:

X-Alk-$R_0$ wherein:
X is a leaving group,
Alk is an alkylene group, and
$R_0$ is —CH(OH)—$CH_2$—$SO_3M$ with M being an alkaline metal.

Preferred X, Alk and M to make the (di)sultaine amine are the same as the ones preferred to make the (di)betaine amine.

The certain aryl alkyl amine of formula (III) that is advantageously used as reactant, has the following formula (III'''):

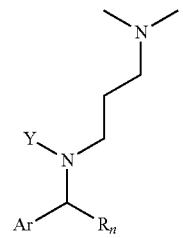

(III''')

wherein $R_n$ have the same meaning as $R_n$ of the aryl aliphatic ketone K of formula (I).

Then, at least one (di)betaine of formula (XVIIa) and/or at least one (di)sultaine of formula (XVIIb) can be prepared from at least one amine of formula (III''') according to the following scheme:

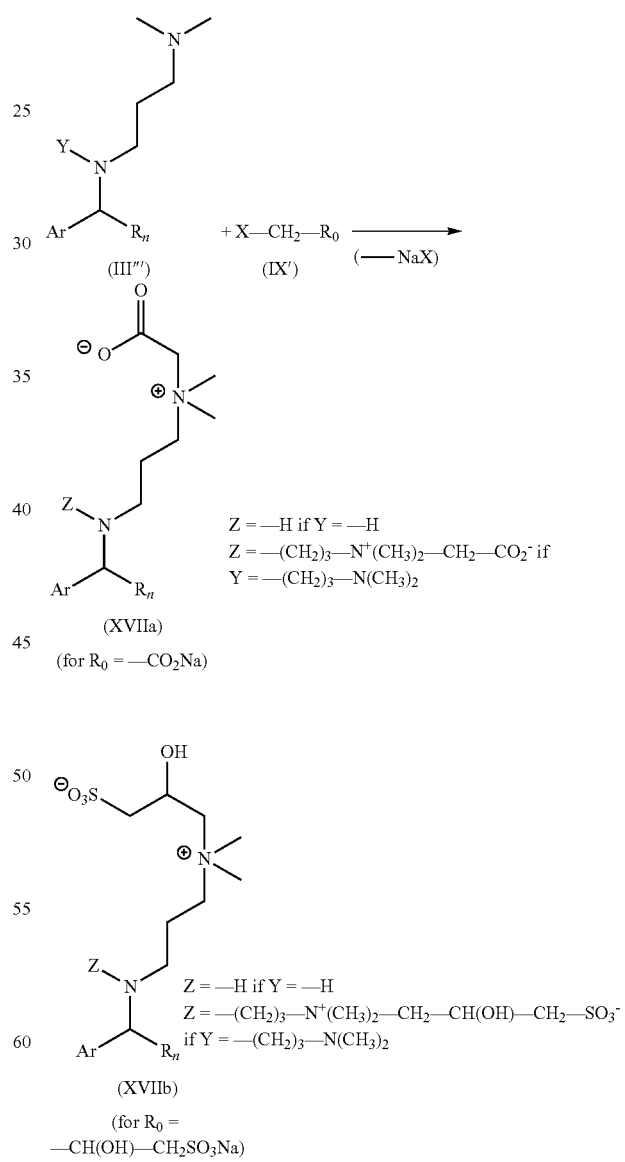

In the above reaction scheme, X is as previously defined.

In the tert-amino amine of formula (III') Y is either hydrogen or 3-dimethylaminopropyl fragment (—$CH_2$—$CH_2$—$CH_2$—$N(CH_3)_2$);

In the (di)betaine (XVIIa) Z is hydrogen when Y is hydrogen and Z is the (—$CH_2$—$CH_2$—$CH_2$—$N^+(CH_3)_2$—$CH_2$—$CO_2^-$) fragment when Y is 3-dimethylaminopropyl fragment (—$CH_2CH_2CH_2$—$N(CH_3)_2$).

In the (di)sultaine (XVIIb) Z is hydrogen when Y is hydrogen and Z is the (—$CH_2$—$CH_2$—$CH_2$—$N^+(CH_3)_2$—$CH_2$—$CH(OH)$—$CH_2$—$SO_3^-$) fragment when Y is 3-dimethylaminopropyl fragment (—$CH_2CH_2CH_2$—$N(CH_3)_2$).

The amine (III''') obtained according to part 1.1 from the aryl aliphatic K (I) is reacted with the alkylating compound (IX') to afford the betaine (XVIIa) or the sultaine (XVIIb) depending on the nature of (IX').

Betaine (XVIIa) is obtained when $R_0$ is —$CO_2Na$ and sultaine (XVIIb) is obtained when $R_0$=—$CH(OH)$—$CH_2$—$SO_3Na$. A mixture of betaine and sultaine is obtained when using a mixture of reagents (IX') including at least one reagent wherein $R_0$ is —$CO_2Na$ and at least one reagent wherein $R_0$=—$CH(OH)$—$CH_2$—$SO_3Na$.

The reaction is usually conducted by contacting the reactants in a reaction zone at temperature from 15° C. to 400° C. and optionally in the presence of an added solvent. As examples of suitable solvents, one can mention methanol, ethanol, isopropanol, DMSO, acetonitrile, water, THF, dioxane and mixtures thereof.

In a preferred embodiment, the pH of the reaction mixture is maintained during the course of the reaction from 8.5 and 9.5. This adjustment can be done by adding required amounts of concentrated NaOH and/or HCl aqueous solutions to the reaction medium during the course of the reaction.

5.2) Synthesis of Betaine Derivatives (XVIII) and Sultaine (XIX) Derivatives

At least one (di)betaine and/or at least one (di)sultaine can be obtained from at least one ketone having its non-aromatic carbonyl-adjacent carbon atom substituted by one or two tert-amine-containing group(s), in particular from at least one ketone of formula (Va) and/or at least one ketone of formula (Vb), the preparation of which from the aryl aliphatic ketone K of formula (I) has been described in part 1.2.

At least one dibetaine and/or at least one disultaine can be obtained from at least one ketone having its non-aromatic carbonyl-adjacent carbon atom substituted by two amine-containing groups, in particular from at least one ketone of formula (Vb), the preparation of which from the aryl aliphatic ketone K of formula (I) has been described in part 1.2.

At least one monobetaine and/or at least one monosultaine can be obtained from at least one ketone having its non-aromatic carbonyl-adjacent carbon atom substituted by one (and only one) tert-amino-containing group, in particular from at least one ketone of formula (Va), the preparation of which from the aryl aliphatic ketone K of formula (I) has already been described in part 1.2.

To this effect, the following reaction scheme can be followed:

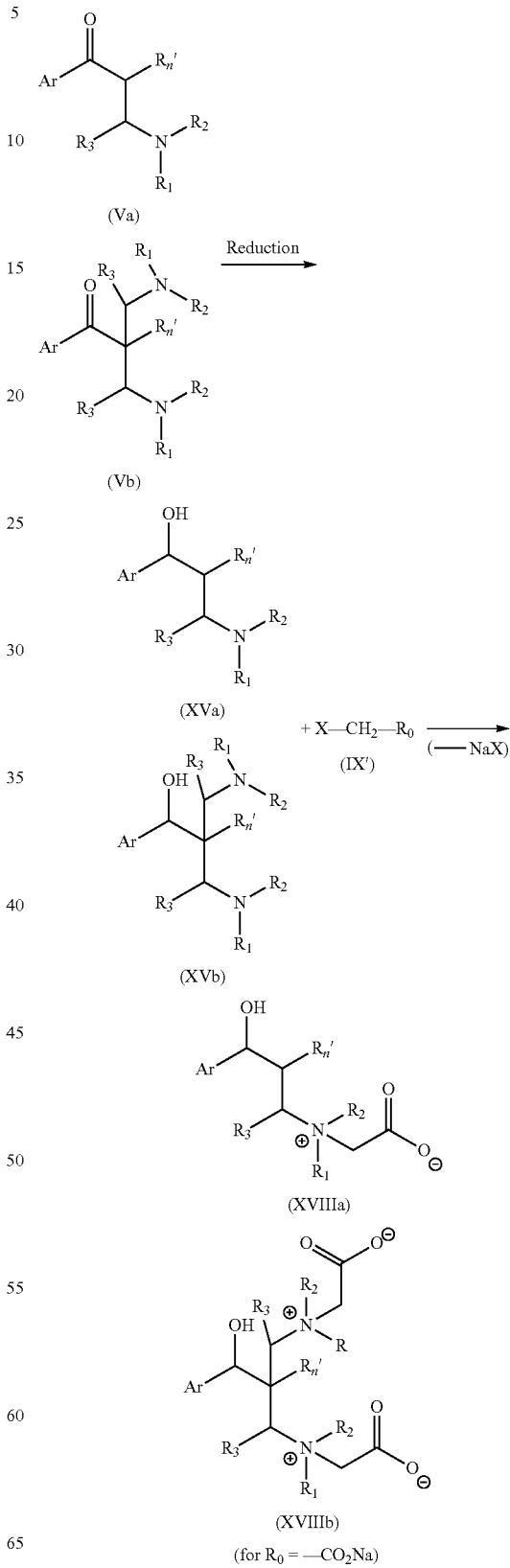

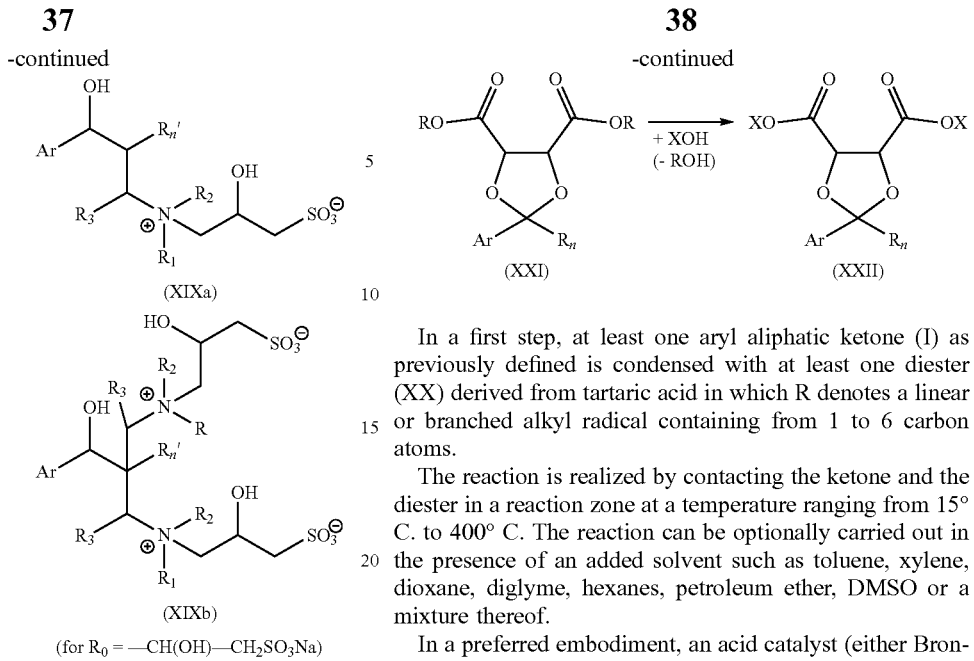

(XIXa)

(XIXb)

(for $R_0 = $ —CH(OH)—CH$_2$SO$_3$Na)

The first step is identical as in part 4.2.

The second step is carried out as in part 5.1.

Betaine (XVIII) or sultaine (XIX) is obtained depending on the nature of $R_0$ in the alkylating agent (IX').

$R_1$, $R_2$ and $R_3$ have the same definition as in part 2.2.

6—Making Anionic Surfactants from Aryl Aliphatic Ketones K

The end compound can be an anionic surfactant.

6.1) Synthesis of Dicarboxylate Salt Derivatives

For example, it can be a dicarboxylate salt derivative of formula

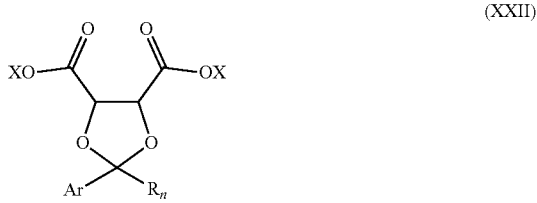

(XXII)

wherein X denotes respectively a monovalent metal cation, an ammonium or a phosphonium cation, or a divalent metal cation. For example, X is Li, Na, K, Cs, NH$_4$, triethanolammonium, Mg or Ca. In particular, X is Li, Na or K.

The following reaction scheme can be followed:

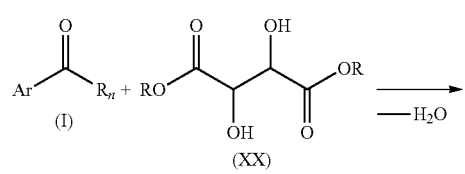

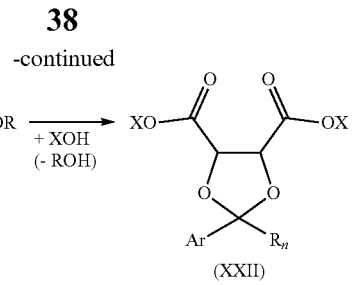

In a first step, at least one aryl aliphatic ketone (I) as previously defined is condensed with at least one diester (XX) derived from tartaric acid in which R denotes a linear or branched alkyl radical containing from 1 to 6 carbon atoms.

The reaction is realized by contacting the ketone and the diester in a reaction zone at a temperature ranging from 15° C. to 400° C. The reaction can be optionally carried out in the presence of an added solvent such as toluene, xylene, dioxane, diglyme, hexanes, petroleum ether, DMSO or a mixture thereof.

In a preferred embodiment, an acid catalyst (either Bronsted or Lewis acid) is employed to accelerate the reaction. One can mention for example H$_2$SO$_4$, HCl, triflic acid, p-toluenesulfonic acid, AlCl$_3$, metal triflate compounds such as aluminium triflate, bismuth triflate, heterogeneous solid acids such as Amberlyst resins and zeolithes.

The water generated during the reaction can be trapped thanks to a Dean-Stark apparatus in order to displace the reaction equilibrium toward the formation of intermediate product (XXI).

At the end of the reaction, this intermediate (XXI) can be isolated after solvent and catalyst removal using standard work-up techniques well known by the skilled person of the art so that no further detail needs to be given here.

In a second step, the ketal diester (XXI) is saponified by conducting the reaction in a basic aqueous X(OH)$_n$ solution wherein n is 1 or 2 and wherein X denotes respectively a monovalent metal cation, an ammonium or a phosphonium cation or a divalent metal cation. In particular X is Li, Na, K, Cs, NH$_4$, triethanolammonium, Mg or Ca. Saponification is conducted at a temperature ranging from 15° C. to 400° C. to afford the final ketal carboxylate product (XXII) along with R—OH as by-product.

6.2) Synthesis of Sulfonate Salt Derivatives

In a first step, at least one aryl aliphatic ketone (I) as previously defined is engaged in a sulfonation reaction using standard techniques known by the skilled person such as falling film reactor sulfonation. The sulfonation can be conducted using gaseous SO$_3$ as the sulfonating agent, preferably diluted in dry air or dry nitrogen. The reaction can be conducted at temperatures ranging from −20° C. to 200° C. Other sulfonating agent such as chlorosulfonic acid (HSO$_3$Cl), oleum or sulfamic acid can also be used.

The reaction can be optionally carried out in the presence of an added solvent such as CH$_2$Cl$_2$, CHCl$_3$, CCl$_4$, dioxane, diglyme, THF, methylTHF or mixture thereof.

An ageing step can be optionally included after sulfonation step in order to achieve full conversion to the sulfonic acid. Such ageing step can be conducted at a temperature between 15° C. to 200° C. The obtained sulfonic acid is then neutralized using an aqueous solution of XOH or X(OH)$_2$, wherein X can be Li, Na, K, Cs, NH$_4$, triethanolammonium, Mg or Ca in order to obtain the sulfonate salt (XXIII).

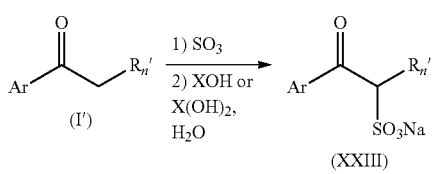

7—Making Non-Ionic Surfactants from Aryl Aliphatic Ketones K

The end compound can be a non-ionic surfactant.

7.1) First Synthesis of Non-Ionic Surfactants

The reaction scheme here below can be followed:

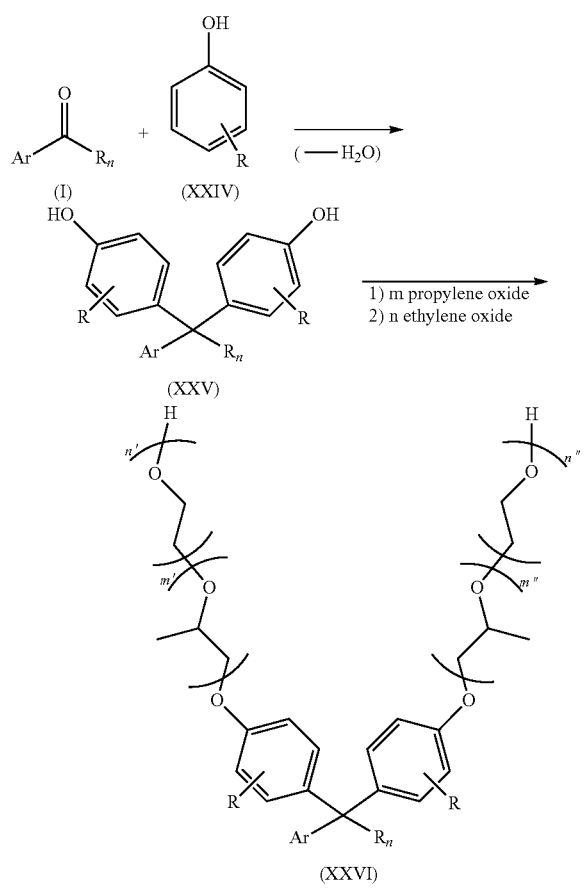

Accordingly, in a first step, at least one ketone (I) is first condensed with 2 equivalents of a substituted or unsubstituted phenolic compound (XXIV) (e.g. when R is nil, (XXIV) is phenol, while when R is methyl or methoxy, (XXIV) can be respectively cresol or guaiacol) in order to afford the bi-phenolic derivative (XXV).

The reaction can be carried out by contacting both reactants in a reaction zone at a temperature ranging from 15° C. to 400° C. optionally in the presence of an added solvent. An excess of the phenolic derivative (XXIV) can be used for this reaction and the reactant in excess can be removed later during the subsequent work-up and recycled.

An acid catalyst (either Bronsted or Lewis acid) can be employed to accelerate the reaction. One can mention for example $H_2SO_4$, HCl, triflic acid, p-toluenesulfonic acid, $AlCl_3$, metal triflate compounds such as aluminium triflate and bismuth triflate, heterogeneous solid acids such as Amberlyst resins, zeolithes, etc.

Water generated during this step can be trapped thanks to a Dean-Stark apparatus is order to drive the reaction equilibrium toward the desired product (XXV).

The intermediate product (XXV) can be isolated using standard work-up techniques well known by the skilled person of the art so that no further detail needs to be given here.

In a second step, the di-phenolic derivative (XXIV) is condensed with m equivalents of propylene oxide and/or with n equivalents of ethylene oxide using standard conditions for alkoxylation of phenolic derivatives in order to afford the non-ionic surfactant (XXVI).

In the above scheme, "1) m propylene oxide|2) n ethylene oxide" should be broadly understood, not implying that both propoxylation and ethoxylation must take place (otherwise said, m or n can be equal to 0 but m and n cannot be both equal to 0 at the same time), a fortiori not implying that propoxylation must take place before ethoxylation, although this is an embodiment that may be preferred.

Other non-ionic surfactants than (XXVI) can be prepared according to the same reaction scheme but using another phenol than (XXIV) as reagent.

As examples of other phenols, one can mention naphtols and aromatic diols such as catechol and resorcinol.

The end compound can be a compound of formula (XXVI) wherein:

m and n are integers ranging from 0 to 50 with the proviso that at least one of m and n is of at least 1, m'+m"=m and n'+n"=n $R_n$ is as defined in part 1.1, R is nil (meaning that there is no substituent on the benzene rings) or R is at least one linear or branched $C_1$-$C_{24}$ hydrocarbon group that can be optionally substituted and/or interrupted by one or more heteroatom(s) or heteroatom(s) containing groups. For example R can be an alkoxy group containing between 1 and 24 carbon atoms.

By specifying that R can be "at least one linear or branched hydrocarbon group", it is intended to denote that the benzene rings of compound (XXV) can be substituted not only by one substituent but also by several one linear or branched hydrocarbon substituents.

Two examples of possible R substituents are methyl and methoxy.

7.2) Second Synthesis of Non-Ionic Surfactants

The end compound can be a non-ionic surfactant of formula (XXVIIIa)

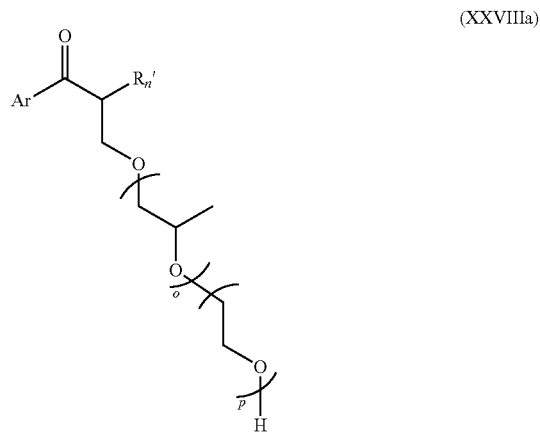

or a non-ionic surfactant of formula (XXVIIIb)

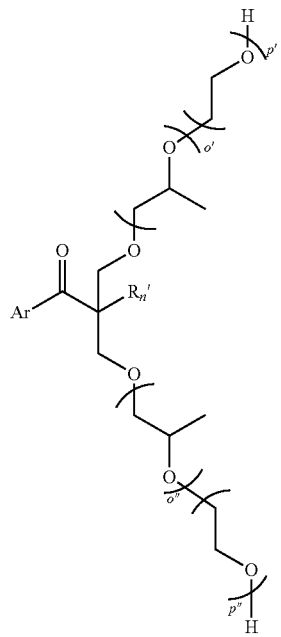

wherein:

R'$_n$ represents an aliphatic group, generally a C$_2$-C$_{26}$ aliphatic group, very often a C$_2$-C$_{18}$ group, often a C$_5$-C$_{16}$ group, o, o', o", p, p' and p" are as defined hereinafter.

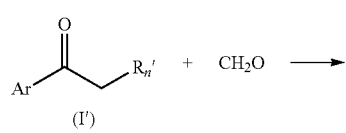

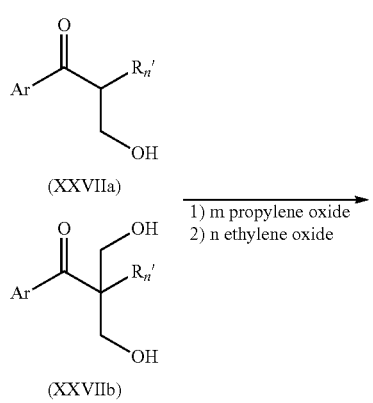

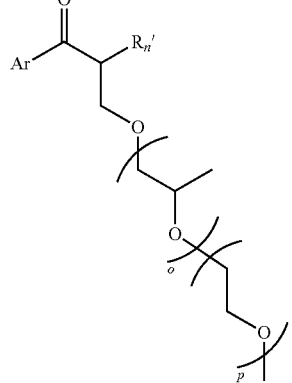

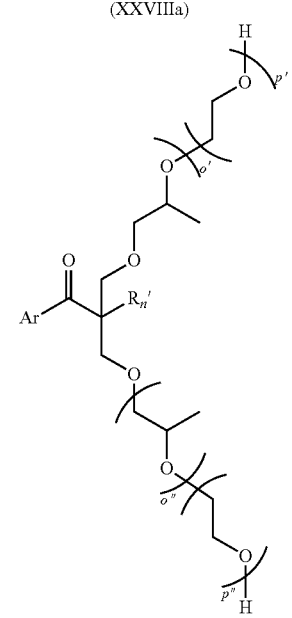

In the above scheme, "1) m propylene oxide|2) n ethylene oxide" should be broadly understood, not implying that both propoxylation and ethoxylation must take place (otherwise said, m or n can be equal to 0 but m and n cannot be both equal to 0 at the same time), a fortiori not implying that propoxylation must take place before ethoxylation, although this is an embodiment that may be preferred.

In a first step, at least one ketone (I') is condensed with formaldehyde (CH$_2$O). The condensation takes advantageously place in a reaction zone at a temperature ranging from −20° C. to 400° C. The reaction can be carried out in the presence of a basic catalyst, such as for example NaOH, KOH, MgO, Na$_2$CO$_3$, NaOMe, NaOEt, tBuOK or NEt$_3$. The reaction can optionally be carried out in a solvent such as methanol, ethanol, isopropanol, DMSO, THF, methyltetrahydrofuran, toluene, a xylene, water, dioxane or a mixture thereof.

For this first reaction step, formaldehyde can be used in excess and the reactant in excess can be recovered and recycled.

The aldol products (XXVIIa), (XXVIIb) or their mixture can be isolated using standard work-up techniques well known by the skilled person of the art.

In the second step, at least one product (XXVIIa) and/or (XXVIIb) is/are condensed with m+n equivalents of alkylene oxide (m equivalents of propylene oxide and/or n equivalents of ethylene oxide, e.g. m equivalents of propylene oxide followed by n equivalents of ethylene oxide) using standard conditions for alkoxylation of alcohols in order to afford the non-ionic surfactants (XXVIIIa) and/or (XXVIIIb).

In the above equation scheme, m and n are integers ranging from 0 to 50 but m and n cannot be both equal to 0.

o, p, o', p', o" and p" are integers ranging from 0 to 50 and the following equalities must be respected:

$$o+o'+o''=m$$

$$p+p'+p''=n$$

7.3) Third Synthesis of Non-Ionic Surfactants

The end compound can be a compound of formula (XXXa) or (XXXb).

(XXXa)

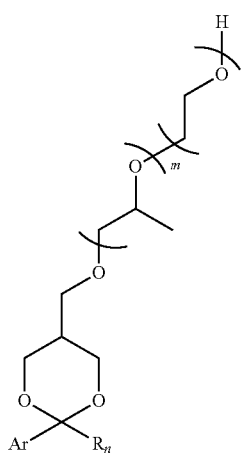

(XXXb)

wherein:

$R_n$ is as defined in part 1.1, m and n are as defined hereinafter.

To this end, in a first step, at least one aryl aliphatic ketone K (I) is condensed with glycerol to afford at least one intermediate as a mixture of 2 isomers (XXIXa) or (XXIXb).

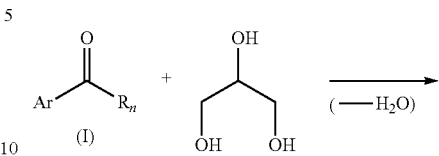

(I)

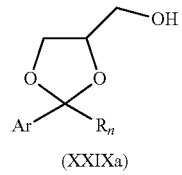

(XXIXa)

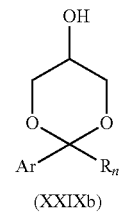

(XXIXb)

This reaction is advantageously carried out by contacting both reactants in a reaction zone at a temperature ranging from 15° C. to 400° C. The reaction can be optionally carried out in the presence of an added solvent such as toluene, xylene, dioxane, diglyme, hexane, petroleum ether, DMSO or a mixture thereof.

In a preferred embodiment, an acid catalyst (either Bronsted or Lewis acid) is employed to accelerate the reaction. One can mention for example: $H_2SO_4$, HCl, triflic acid, p-toluenesulfonic acid, $AlCl_3$, metal triflate compounds such as aluminium triflate, bismuth triflate, heterogeneous solid acids such as Amberlyst resins, zeolithes, etc.

The water generated during the reaction can be trapped thanks to a Dean-Stark apparatus in order to displace the reaction equilibrium toward the formation of the at least one intermediate as a mixture of the 2 isomers (XXIXa) and (XXIXb).

At the end of the reaction, this mixture of the 2 isomers (XXIXa) and (XXIXb) can be isolated after solvent and catalyst removal using standard work-up techniques well known by the skilled person of the art so that no further detail needs to be given here.

In the second step, the at least one intermediate as a mixture of the 2 isomers (XXIXa) and (XXIXb) is condensed with m+n equivalents of alkylene oxide (m equivalents of propylene oxide and/or n equivalents of ethylene oxide, e.g. m equivalents of propylene oxide followed by n equivalents of ethylene oxide) using standard conditions for alkoxylation of alcohols in order to afford the non-ionic surfactants as a mixture of 2 isomers (XXXa) and (XXXb).

The reaction taking place in the second step can be represented as follows:

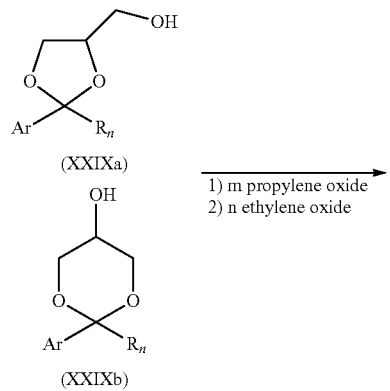

(XXIXa)

(XXIXb)

1) m propylene oxide
2) n ethylene oxide

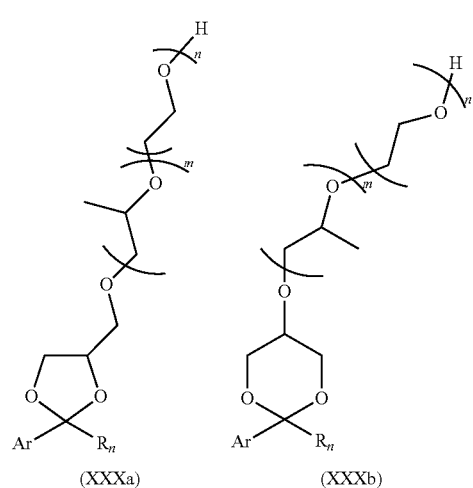

(XXXa)  (XXXb)

In the above reaction scheme, "1) m propylene oxide|2) n ethylene oxide" should be broadly understood, not implying that both propoxylation and ethoxylation must take place (otherwise said, m or n can be equal to 0 but both and m and n cannot be at the same time equal to 0), a fortiori not implying that propoxylation must take place before ethoxylation, although this is an embodiment that may be preferred.

As a matter of fact, in the above reaction scheme, m and n are integers ranging from 0 to 50 provided at least one of m and n is of at least 1.

7.4) Fourth Synthesis of Non-Ionic Surfactants

The end compound can be a compound of formula (XXXII)

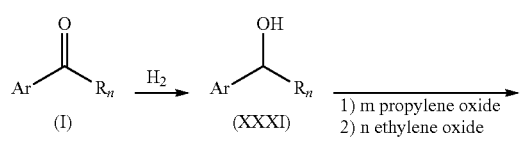

(I)  (XXXI)

1) m propylene oxide
2) n ethylene oxide

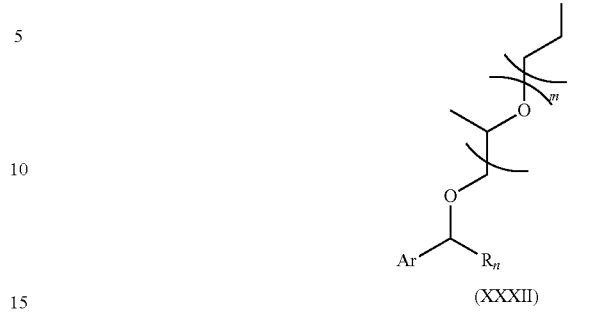

(XXXII)

wherein:

$R_n$ is as defined in part 1.1, m and n are as defined hereinafter.

To this end, in a first step, at least one aryl aliphatic ketone K (I) is hydrogenated using gaseous dihydrogen to afford at least one alcohol derivative (XXXI). The reaction can be performed in an autoclave under hydrogen pressure at a temperature ranging from 15° C. to 400° C. at a pressure ranging from 1 atm to 200 bar. The reaction is usually conducted with a transition metal (for example Ni, Co, Cu, Fe, Rh, Ru, Ir, Pd and Pt) based catalyst (typically Pd/C). The reaction can be optionally carried out in the presence of an added solvent such as methanol, ethanol, isopropanol, tert-butanol, THF, 2-methyltetrahydrofuran, dioxane, dimethoxyethane, diglyme, water and mixtures thereof.

The obtained carbinol (XXXI) is then condensed with with m+n equivalents of alkylene oxide (m equivalents of propylene oxide and/or n equivalents of ethylene oxide, e.g. m equivalents of propylene oxide followed by n equivalents of ethylene oxide) using standard conditions for alkoxylation of alcohols in order to afford the non-ionic surfactants (XXXII).

In the above reaction scheme, "1) m propylene oxide|2) n ethylene oxide" should be broadly understood, not implying that both propoxylation and ethoxylation must take place (otherwise said, m or n can be equal to 0 but both m and n cannot be at the same time equal to 0), a fortiori not implying that propoxylation must take place before ethoxylation, although this is an embodiment that may be preferred.

As a matter of fact, in the above reaction scheme, m and n are integers ranging from 0 to 50 provided at least one of m and n is of at least 1.

8—Making Monomers and Intermediates from Aryl Aliphatic Ketones K 8.1) Synthesis of a First Monomer The at least one end compound can be a compound of formula (XXXIV). Such a compound, which contains an ethylenic carbon-carbon double bond, is suitable to undergo a radical polymerization.

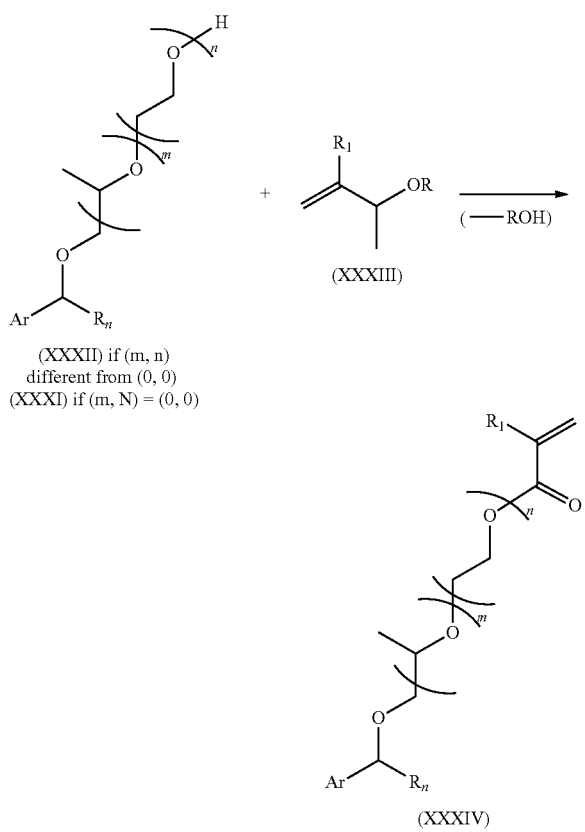

(XXXII) if (m, n) different from (0, 0)
(XXXI) if (m, N) = (0, 0)

(XXXIII)

(XXXIV)

$R_n$ is as defined in part 1.1, and m and n are integers ranging from 0 to 50.

In some embodiments, in compound of formula (XXXIV) m and n can be both equal to 0. In this case the starting alcohol used to obtain (XXXIV) is (XXXI) in the above scheme.

In the case where (m,n)≠(0,0) in (XXXIV), the starting alcohol used to obtain (XXXIV) is (XXXII).

In the above reaction scheme, the substituent $R_1$ is selected from hydrogen and a linear or branched hydrocarbon radical having from 1 to 24 carbon atoms which can be optionally substituted and/or interrupted by one or more heteroatoms or heteroatom containing groups. For example, $R_1$ can be H, methyl, ethyl, propyl, isopropyl, butyl, sec-butyl, isobutyl or tert-butyl.

In the above reaction scheme, the substituent R is selected from a linear or branched hydrocarbon radical having from 1 to 24 carbon atoms which can be optionally substituted and/or interrupted by one or more heteroatoms or heteroatom containing groups. For example, R can be selected from —$CH_3$, —$CH_2CH_3$, propyl, isopropyl, butyl, sec-butyl, isobutyl and tert-butyl.

The substituent R can also be an acyl radical —(OC)—R' where R' is a linear or branched hydrocarbon radical containing between 1 to 26 carbon atoms which can be optionally substituted and/or interrupted by one or more heteroatom or heteroatom containing group. Preferably R' is $CH_2$=$CR_1$— and in this case the compound (XXXIII) is the anhydride derived from $CH_2$=$CR_1$—$CO_2H$.

The ethoxylated intermediate (XXXII) or the alcohol (XXXI) obtained from aryl aliphatic ketone (I) according to the reaction scheme described in paragraph 7.4 is reacted with at least one acrylate derivative (XXXIII) according to a transesterification reaction in order to afford at least one other acrylate derivative (XXXIV).

This last reaction is advantageously carried out by contacting both reactants in a reaction zone at a temperature ranging from 15° C. to 400° C.

The reaction can be catalyzed either by acids or by bases. As example of suitable acids, one can mention $H_2SO_4$, HCl, triflic acid, p-toluenesulfonic acid, $AlCl_3$, metal triflate compounds such as aluminium triflate, bismuth triflate, heterogeneous solid acids such as Amberlyst resins, zeolithes etc. As examples of suitable bases, one can mention NaOH, KOH, MgO, $Na_2CO_3$, NaOMe, NaOEt, tBuOK or $NEt_3$.

The reaction can be carried out in a suitable solvent such as methanol, ethanol, isopropanol, DMSO, THF, methyltetrahydrofuran, toluene, xylenes, water, dioxane or a mixture thereof.

The acrylate derivative (XXXIII) can be added progressively in the reaction medium in order to avoid side-polymerization to occur.

8.2) Synthesis of a Second Monomer

The at least one end compound can be a compound of formula (XXXV)

Such a compound, which also contains an ethylenic carbon-carbon double bond, is likewise suitable to undergo a radical polymerization.

It can be prepared from an aryl alkyl amine of formula (III), wherein:

$R_n$ is as defined in part 1.1;

$R_2$ is selected from hydrogen or a linear or branched hydrocarbon radical having 1 to 24 carbon atoms which can be optionally substituted and/or interrupted by one or more heteroatoms or hereroatom containing groups; for example, $R_2$ can be selected from H, —$CH_3$, —$CH_2CH_3$, propyl, isopropyl, butyl, sec-butyl, isobutyl and tert-butyl.

At least one aryl alkylamine (III) prepared according to part 1.1 is reacted with at least one acrylate derivative (XXXIII) under suitable conditions that prevent conjugate addition to occur in order to afford at least one acrylamide (XXXV).

The reaction scheme is as follows:

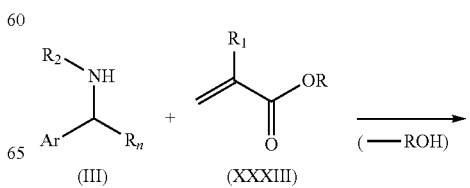

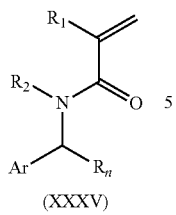

(XXXV)

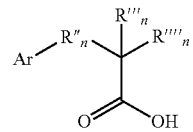

(XXXVI)

In compounds (XXXIII) and (XXXV), R and $R_1$ have the same meaning as in part 8.1.

The reaction is advantageously carried out by contacting both reactants in a reaction zone at a temperature ranging from 15° C. to 400° C.

The reaction can be catalyzed by acids or bases. As example of suitable acids one can mention $H_2SO_4$, HCl, triflic acid, p-toluenesulfonic acid, $AlCl_3$, metal triflate compounds (such as aluminium triflate, bismuth triflate), heterogeneous solid acids such as Amberlyst resins, zeolithes, etc. As examples of suitable bases, one can mention NaOH, KOH, MgO, $Na_2CO_3$, NaOMe, NaOEt, tBuOK, $NEt_3$ etc.

The reaction can be carried out in a suitable solvent such as methanol, ethanol, isopropanol, DMSO, THF, methyltetrahydrofuran, toluene, xylenes, water, dioxane or a mixture thereof.

As an alcohol ROH is generated during the reaction as a side product, it can be removed thanks to distillation in order to drive the reaction toward the desired product (XXXV).

The acrylate derivative (XXXIII) can be added progressively in the reaction medium in order to avoid side-polymerization to occur.

8.4) Synthesis of a Branched Fatty Acid

The end compound can be a branched fatty acid of formula (XXXVI), as obtainable by the following reaction:

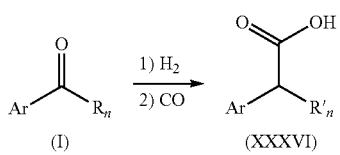

In a first stage, at least one ketone (I) with $R_n$ being defined as in part 1.1 is hydrogenated to afford the corresponding secondary alcohol. Standard hydrogenation conditions can be used.

This alcohol is then engaged in a carbonylation reaction to afford at least one end product (XXXVI).

The carbonylation reaction is advantageously carried out by reacting the secondary alcohol under a CO pressure (typically from 1 atm to 200 bar), in a reaction zone at a temperature usually ranging from 15° C. to 400° C.

The reaction can be optionally carried out in the presence of a suitable solvent and the skilled person of the art will choose the most suitable solvent. Importantly, the reaction can be catalyzed by transition metal based catalysts (for example Co, Rh, Ir and Pd based homogeneous catalyst).

Usually, a halide based promoter is necessary for the reaction to occur. Preferably, the promoter is an iodide, such as HI.

Importantly, during the reaction significant isomerization may occur and mixture of isomeric products (XXXVI) may be obtained. The isomeric products can be represented by the formula:

In the above formula $R''_n$ is a divalent hydrocarbon radical that can be optionally substituted and/or interrupted by heteroatoms and/or heteroatom containing substituents and $R'''_n$, $R''''_n$ are independently hydrogen or hydrocarbon radicals that can be optionally substituted and/or interrupted by heteroatoms and/or heteroatom containing substituents. $R''_n$, $R'''_n$ and $R''''_n$ are derived from the $R_n$ substituent contained in the starting material (I) and the sum of the number of carbon atoms contained in $R''_n$, $R'''_n$ and $R''''_n$ must be equal to the number of carbon atoms contained in R.

8.5) Synthesis of Polyamines

The end compound can be a polyamine, especially a polyamine of formula (XXXVIII):

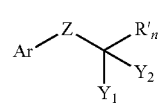

(XXXVIII)

Such a polyamine can be prepared using at least one aryl aliphatic ketone (I') as starting material, with $R'_n$ being defined as in part 1.2, according to the following reaction scheme:

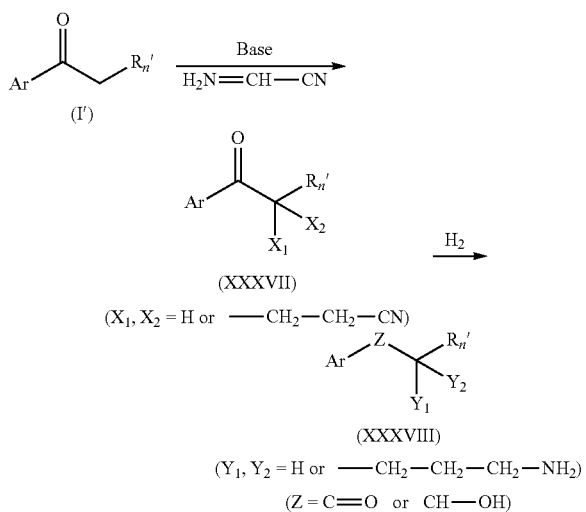

$X_1$ and $X_2$ independently represent a hydrogen atom or —$CH_2$—$CH_2$—CN but all cannot be hydrogen, meaning that at least one of $X_1$ and $X_2$ is —$CH_2$—$CH_2$—CN.

$Y_1$ and $Y_2$ independently represent a hydrogen atom or —$CH_2$—$CH_2$—$CH_2$—$NH_2$ but all cannot be hydrogen, meaning that at least one of $Y_1$ and $Y_2$ is —$CH_2$—$CH_2$—$CH_2$—$NH_2$.

Z can be either a carbonyl group (C=O) or a carbinol (CH—OH) group or a mixture thereof.

Thus, at least one aryl aliphatic ketone (I') is first condensed with acrylonitrile to afford at least one intermediate of formula (XXXVII).

The reaction is advantageously carried out by contacting both reactants in a reaction zone at a temperature ranging generally from 15° C. to 400° C. and in the presence of an optional solvent such as methanol, ethanol, isopropanol, DMSO, THF, methyltetrahydrofuran, toluene, xylene, water, dioxane or a mixture thereof.

The reaction can be catalyzed by a suitable base such as for example NaOH, KOH, MgO, $Na_2CO_3$, NaOMe, NaOEt, tBuOK or $NEt_3$.

Optionally and possibly preferably, the reaction is carried out by adding acrylonitrile progressively in the reaction medium in order to avoid side polymerizations, and acrylonitrile can be used in stoichiometric excess. The acrylonitrile in excess can be recovered and recycled.

Mixture of products (XXXVII) with different substituents $X_n$ (n=1 to 2) can be obtained.

In a second step, at least one (poly)nitrile derivative (XXXVII) is hydrogenated to afford the at least one corresponding (poly)amine (XXXVIII). Usually, standard conditions for nitrile hydrogenation are used, for example under hydrogen pressure ranging from 1 atm to 200 bar, at a temperature ranging from 15° C. to 400° C., in the presence of an optional solvent and using advantageously a transition metal based catalyst (e.g. Nickel Raney).

A mixture of products (XXXVIII) with different $Y_n$ (n=1 to 2) and Z groups can be obtained.

8.5) Synthesis of Esters

The end compound can be an ester of formula (XL), as obtainable by the following reaction:

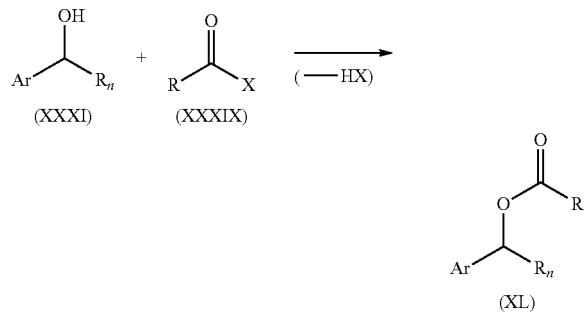

The carbinol (XXXI) prepared according to section 7.4 is reacted with the carboxylic acid (XXXIX) (if X=—OH) or the carboxylic acid derivative such as ester (if X=—OR' where R' is a linear or branched hydrocarbon radical containing between 1 to 6 carbon atoms which can be optionally substituted and/or interrupted by one or more heteroatom or heteroatom containing group), anhydride (if X=—$O_2C$—R' where R' is a linear or branched hydrocarbon radical containing between 1 to 6 carbon atoms which can be optionally substituted and/or interrupted by one or more heteroatom or heteroatom containing group, preferably R' is the same as R), acyl halide (if X is an halide atom such as fluoride chloride, bromide or iodide) under suitable reaction conditions to afford the ester derivative (XL).

Suitable esterification conditions are well known by the person skilled in the art so that no further detail needs to be given here.

In the formula above, R is hydrogen or a linear or branched hydrocarbon radical having 1 to 6 carbon atoms which can be optionally substituted and/or interrupted by one or more heteroatoms or hereroatom containing groups.

X is selected among:
hydroxyl group, alkoxy group —OR' where R' is a linear or branched hydrocarbon radical containing between 1 to 6 carbon atoms which can be optionally substituted and/or interrupted by one or more heteroatom or heteroatom containing group.

(Alkyl)carboxy group —$O_2C$—R' where R' is a linear or branched hydrocarbon radical containing between 1 to 6 carbon atoms which can be optionally substituted and/or interrupted by one or more heteroatom or heteroatom containing group. R' can be identical to R.

halogen such as: —F, —Cl, —Br and —I.

$R_n$ has the same meaning as in section 1.1.

8.5) Synthesis of Amides

The end compound can be an amine of formula (XLI), as obtainable by the following reaction:

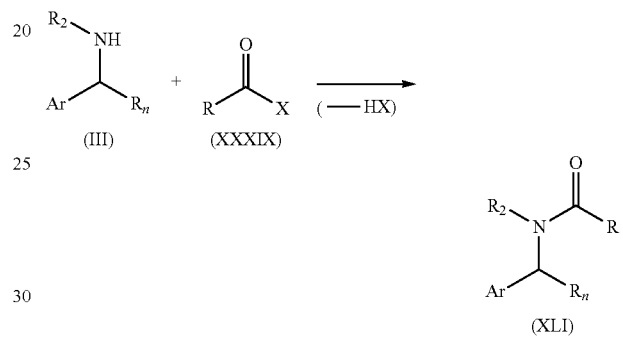

The amine (III) described in section 7.4 is reacted with the carboxylic acid derivative (XXXIX) described in section 8.4 under suitable reaction conditions to arrive to the amide derivative (XLI).

Suitable conditions for amide synthesis are well known by the person skilled in the art so that no further detail needs to be given here.

In the formula above, R and X have the same meaning as in section 8.4, $R_2$ has the same meaning as in section 8.2 and $R_n$ the same as in section 1.1.

8.5) Synthesis of Oximes

The end compound can be an oxime of formula (XLII), as obtainable by the following reaction:

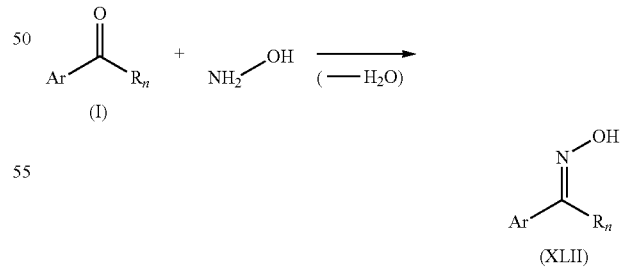

The aryl aliphatic ketone (I) is condensed with hydroxylamine in order to obtain the oxime (XLII).

Suitable conditions for oxime synthesis are well known by the person skilled in the art so that no further detail needs to be given here.

In the formula above, $R_n$ has the same meaning as in section 1.1.

Aromatic substituents Ar of particular interest are furan-2-yl, 2-pyridyl, 2-hydroxyphenyl and 2-aminophenyl.

9—Making Secondary Alcohols, Olefins and Olefin Sulfonates from Aryl Aliphatic Ketones K 9.1) Use of the Aryl Aliphatic Ketone for the Synthesis of Secondary Alcohols The aryl aliphatic ketones obtained in accordance with the process P are advantageously used for the manufacture of respective secondary alcohols. To obtain these alcohols the aryl aliphatic ketones obtained in the process P are subjected to a hydrogenation reaction. The reaction is usually carried out using heterogeneous transition metal catalysts on a support in an autoclave with hydrogen gas as hydrogenating agent.

Just by way of example palladium catalysts supported on carbon materials may be mentioned as catalysts. The hydrogenation reaction is usually carried out at a hydrogen pressure of from 500 to 5000 kPa and at a temperature in the range of from 120 to 200° C. without the use of an added solvent.

9.2) Use of the Secondary Alcohols for the Synthesis of Olefins

The secondary alcohols obtained as described above may be further converted to olefins by a dehydration reaction.

Preferably, the dehydration is carried out in the substantial absence of an added solvent, preferably in the absence of added solvent, using aluminum oxide, preferably $\eta$-$Al_2O_3$ as catalyst at a temperature in the range of from 250 to 350° C. and for a time of 30 min to 6 h.

The dehydration reaction is usually carried out in an inert atmosphere.

9.3) Sulfonation of the Olefins

The olefins manufactured may be further converted into olefin sulfonates.

"Olefin sulfonate" (OS) as used herein means at least one sulfonate compound that can be obtained.

The OS consists generally of at least one monosulfonate or of at least one monosulfonate and at least one polysulfonate.

As herein used, a polysulfonate is intended to denote a di- or higher sulfonate. Disulfonates and higher sulfonates may be formed as byproducts during the sulfonation of olefins followed by the alkaline hydrolysis. A low polysulfonate content in the OS may improve the physical stability of compositions prepared therefrom (no phase separation). In the OS, the polysulfonate content, based on the total weight of the OS, is preferably of at most 2 wt. %, more preferably of at most 1 wt. %. For practical reasons, the lower limit for polysulfonates in the OS is generally no less than 0.0005 wt. %, based on the weight of the OS.

Both hydroxy alkane sulfonates and alkene sulfonates are generally formed during the sulfonation of olefins followed by the alkaline hydrolysis. Thus, the OS is usually a mixture comprising at least one hydroxy alkane sulfonate and at least one alkene sulfonate.

As herein used:
 the terms "hydroxy alkane sulfonate" are intended to denote an alkane that is substituted by at least one hydroxyl group and least one sulfonate (—$SO_3$-group);
 the term "alkene" encompasses compounds comprising one and only one carbon-carbon double bond (mono-olefins) as well as compounds comprising several carbon-carbon double bond (diolefins and higher olefins);
 the terms "alkene sulfonate" are intended to denote an alkene, as above defined, that is substituted by at least one sulfonate (—$SO_3$—) group.

In general, the at least one hydroxy alkane sulfonate is composed of at least one hydroxy alkane monosulfonate, or of at least one hydroxy alkane monosulfonate and at least one hydroxy alkane polysulfonate. Hydroxy alkane di- and higher sulfonates may be formed as byproducts during the sulfonation of olefins followed by the alkaline hydrolysis.

Likewise, the at least one alkene sulfonate is composed of at least one alkene monosulfonate, or of at least one alkene monosulfonate and at least one alkene polysulfonate. Alkene di- and higher sulfonates may be formed as byproducts during the sulfonation of olefins followed by the alkaline hydrolysis.

The at least one hydroxy alkane sulfonate comprised in the OS may be composed of at least one monohydroxy alkane sulfonate or of at least one monohydroxy alkane sulfonate and at least one polyhydroxy alkane polysulfonate. Preferably, the hydroxy alkane sulfonate is free of or is essentially free of polyhydroxy alkane polysulfonates, which ones may be formed by the sulfonation of di- or higher olefins comprised in the olefin manufactured by the dehydration reaction.

The at least one alkene sulfonate comprised in the OS may be composed of at least one mono-olefin sulfonate or of at least one mono-olefin sulfonate and at least one polyolefin sulfonate (which often includes at least one polyolefin polysulfonate). Preferably, the alkene sulfonate is free of, is essentially free of or comprises a low amount of polyolefin polysulfonates, including diolefin disulfonates and/or higher olefin polysulfonates. More generally, it is preferred that the alkene sulfonate be free of, be essentially free of or comprises a low amount of polyolefin sulfonates, including diolefin or higher olefin monosulfonates and polyolefin polysulfonates. Polyolefin sulfonates may be formed as byproducts during the sulfonation of mono-olefins or by the mono- or polysulfonation of polyolefins (di- or higher olefins) comprised in the olefin manufactured by the dehydration reaction.

Still other sulfonates may be formed during the sulfonation of olefins. For example, hydroxy mono-olefin sulfonates may be formed, concurrently with diolefin sulfonates, by the monosulfonation of diolefins comprised in the olefin manufactured by the dehydration reaction. Hydroxy diolefin sulfonates may also be formed as by-products.

A low content of di- or higher olefin sulfonate in the OS may improve the physical stability of the compositions prepared therefrom (no phase separation). Therefore, in the OS, the polyolefin sulfonate content, based on the total weight of the OS, is preferably of at most 2 wt. %, more preferably at most 1 wt. %. For practical reasons, the lower limit for polyolefin sulfonate in the OS is generally no less than 0.0005 wt. %, based on the weight of the OS.

To reduce the formation of polysulfonates, of polyhydroxy polysulfonates and of polyolefin sulfonates (especially of polyolefin polysulfonates), the fatty acid, fatty acid derivative or mixture thereof which is used as starting material of the process P is desirably an alkane carboxylic acid, an alkane carboxylic acid derivative or a mixture thereof.

In the OS, the combined weight amount of hydroxy alkane monosulfonate and mono-olefin monosulfonate, based on the total weight of the OS, is generally of at least 90%, preferably of at least 95%, more preferably at least 98%, still more preferably at least 99%.

In the OS, the weight ratio of hydroxy alkane monosulfonate to mono-olefin sulfonate is quite often greater than 1 and no more than 20. The weight ratio of hydroxy alkane monosulfonate to mono-olefin sulfonate is preferably of at least 3.25 and more preferably of at least 4.5. An OS wherein the weight ratio of hydroxy sulfonate to alkene sulfonate is at of least 3.25 has significantly reduced tendency to physically separate and in most cases forms compositions that are fully physically stable.

Sulfonation of the Olefins

The olefins obtained after the dehydration reaction described above can be sulfonated followed by an alkaline hydrolysis to obtain olefin sulfonates which are useful as surfactants.

To this purpose, the olefin is typically reacted with a sulfonating agent such as sulfur trioxide, sulfuric acid or oleum. Anhydrous $SO_3$ is preferred.

The sultone that is formed is composed of at least one beta-sultone or of at least one beta-sultone and at least one sultone other than a beta-sultone, like a gamma-sultone, a delta-sultone, an epsilon-sultone or a mixture thereof. In general, more than 50 wt. % of the sultone is beta-sultone.

Together with the sultone, an amount of alkene sulfonic acid may be formed as side product.

According to a first embodiment, the sulfonation is carried out in a falling film reactor.

The falling film reactor is advantageously equipped with cooling means in order to prevent or limit temperature increase in the reactor due to the high exothermicity of the reaction. Desirably, the temperature in the reactor does not exceed 80° C.; more desirably, it is of at most 50° C. Then, for example, the reactor may be equipped with a cooling jacket supplied with cold water; the temperature of the cooling jacket is usually set-up at around 0° to 30° C., possibly at around 0° to 10° C.

A gas flow consisting of a mixture of the sulfonating agent (e.g. anhydrous $SO_3$) diluted with an inert gas at a concentration usually in the range of from 0.5 to 10% v/v, preferably of from 1 to 5% v/v (particularly preferred around 2.5% v/v) is preferably contacted with a falling film of the liquid olefin. The inert gas may be nitrogen or air, and it has been advantageously carefully dried before forming the mixture with the sulfonating agent.

The flows of gas and liquid phases are set-up in order to ensure:
- a residence time generally of from 10 seconds to 10 min, preferably of from 1 min to 6 min (e.g. 3 minutes) and
- a mole ratio $SO_3$:olefin generally in the range of from 0.7:1 to 1.5:1, preferably of from 0.8:1 to 1.2:1, more preferably of from 0.9:1 to 1.1:1 and still more preferably of about 1.05:1 in the falling film reactor.

When using a mixture of olefins with different chain lengths (and thus different molecular weights) the total molar flow of olefins can be calculated using the average molecular weight of the mixture of olefins.

According to a 2nd embodiment, a sulfonating reagent which is a complex of a sulfonating agent with an organic solvent is formed in situ in a reactor.

The sulfonation is generally carried out batchwise in the reactor. The reactor is advantageously equipped with a mechanical stirring in the liquid phase.

A complexing organic solvent (possibly, an ether such as dioxane) may be mixed with a non-complexing organic solvent (possibly, a halogenated solvent such as anhydrous trichloromethane) to form an organic solvent mixture.

Alternatively, the complexing organic solvent may be used alone, without being admixed with any non-complexing organic solvent.

The organic solvent mixture or the complexing organic solvent taken alone, as the case may be, is cooled down to a temperature typically in the range of from −10° C. to 25° C., preferably from −5° C. to 10° C.

Then, a liquid sulfonating agent (for example, liquid $SO_3$) is added to the organic solvent mixture or to the complexing organic solvent to generate the sulfonating agent-complexing organic solvent complex. Advantageously, this complex precipitates out from the organic solvent mixture. The addition of the liquid sulfonating agent is desirably made slowly and under stirring. When $SO_3$ is the sulfonating agent and dioxane is the complexing agent, about 2 molar equivalents of $SO_3$ can be used to generate the $SO_3$-dioxane complex.

The olefin is then reacted with the complex sulfonating agent-complexing organic solvent. The reaction is advantageously made under stirring and at a temperature T° of from −10° C. to 15° C., preferably from −5° C. to 10° C.

The molar ratio olefin:sulfonating agent may range from 0.5 to 2 and can be of about 1.

The reaction medium comprising the olefin and the complex sulfonating agent-complexing organic solvent is maintained at temperature T° for a time sufficient for allowing the formation of the sultone. This time may range from 0.3 h to 3 h. The reaction medium may then be allowed to warm up to room temperature (e.g. to a temperature between 15° C. and 30° C.).

All the volatiles (possibly, the complexing organic solvent—e.g. dioxane—or the non-complexing organic solvent—e.g. $CHCl_3$—and the complexing organic solvent—e.g. dioxane —) are then advantageously removed under vacuum.

Optional Aging

Following the sulfonation reaction, the mixture exiting the reactor (composed mainly of beta-sultones) can be allowed to age in order to allow isomerization & trans-sulfonation to occur and to increase the conversion of starting olefins.

During aging, some beta-sultones may be converted into gamma-sultones which may in turn be converted into delta-sultones. Also some beta-sultones may be converted to alkene sulfonic acids.

Alkaline Hydrolysis of the Sultones

In accordance with the process, the sultone is subjected to an alkaline hydrolysis, so as to form the olefin sulfonate.

To this end, the sultone may be fed to a neutralization/hydrolysis unit comprising a reactor. The reactor is preferably equipped with a mechanical stirring.

The neutralization/hydrolysis can be carried out with a water soluble base, such as a hydroxide, a carbonate, a bicarbonate and/or an amine compound. Among the water soluble bases, sodium hydroxide and sodium carbonate can be cited. The corresponding bases derived from potassium or ammonium are also suitable.

The neutralization is generally carried out with excessive base, calculated on the acid component.

Generally, neutralization is carried out at a temperature in the range of from 0° C. to 40° C.

Hydrolysis may be carried out at a temperature above 50° C. up to 250° C., preferably from 80° C. to 200° C.

The hydrolysis time generally may be from 5 minutes to 4 hours.

During this stage of the process, the sultones are transformed into the desired olefin sulfonates through a ring opening reaction.

The sulfonation, digestion and hydrolysis reactions can be followed using NMR analysis. At the end of the process the amount of water in the medium may be adjusted in order to reach an aqueous solution of olefin sulfonates with a desired concentration of active matter.

Valuable Compounds Preparable by the Process P'

It is a last object of the present invention to provide new valuable compounds, with a particular interest for surfactants.

This last object of the present invention is achieved by a variety of compounds, notably surfactants, susceptible of being prepared by the process P' as above described.

Thus, the present invention concerns also:
- a compound of formula (III) as previously described, in particular a compound of formula (III'), a compound of formula (III") or a compound of formula (III''') as previously described;
- a compound of formula (Va) as previously described, a compound of formula (Vb) as previously described or a mixture thereof;
- a compound of formula (VII) as previously described;
- a compound of formula (VIIIa) as previously described, a compound of formula (VIIIb) as previously described or a mixture thereof;
- a compound of formula (X) as previously described;
- a compound or a mixture of compounds of general formula (XIa) as previously described;
- a compound or a mixture of compounds of general formula (XIb) as previously described;
- a compound of a mixture of compounds of general formula (XII) as previously described;
- a compound of a mixture of compounds of general formula (XIIIa) as previously described;
- a compound of a mixture of compounds of general formula (XIIIb) as previously described;
- a compound of formula (XIV) as previously described;
- a compound of formula (XVa) as previously described, a compound of formula (XVb) as previously described or a mixture thereof;
- a compound of formula (XVIa) as previously described, a compound of formula (XVIb) as previously described or a mixture thereof;
- a compound of formula (XVIIa) as previously described;
- a compound of formula (XVIIb) as previously described;
- a compound of formula (XVIIIa) as previously described, a compound of formula (XVIIIb) as previously described or a mixture thereof;
- a compound of formula (XIXa) as previously described, a compound of formula (XIXb) as previously described or a mixture thereof;
- a compound of formula (XXI) as previously described;
- a compound of formula (XXII) as previously described;
- a compound of formula (XXIII) as previously described;
- a compound of formula (XXVI) as previously described;
- a compound of formula (XXVIIa) as previously described, a compound of formula (XXVIIb) as previously described or a mixture thereof;
- a compound of formula (XXVIIIa) as previously described, a compound of formula (XXVIIIb) as previously described or a mixture thereof;
- a compound of formula (XXIXa) as previously described, a compound of formula (XXIXb) as previously described or a mixture thereof;
- a compound of formula (XXXa) as previously described, a compound of formula (XXXb) as previously described or a mixture thereof;
- a compound of formula (XXXI) as previously described;
- a compound of formula (XXXII) as previously described;
- a compound of formula (XXXIV) as previously described;
- a compound or a mixture of compounds of general formula (XXXV) as previously described;
- a compound or or a mixture of compounds of general formula (XXXVI) as previously described; and
- a compound or or a mixture of compounds of general formula (XXXVII) as previously described.
- a compound or or a mixture of compounds of general formula (XXXVIII) as previously described.
- a compound or or a mixture of compounds of general formula (XL) as previously described.
- a compound or or a mixture of compounds of general formula (XLI) as previously described.
- a compound or or a mixture of compounds of general formula (XLII) as previously described.

Summary of the Advantages of the Present Invention

The process P of the present invention thus offers an easy access to aryl aliphatic ketones K. The process P yields the desired ketones in high yield with only minor amounts (if at all) of undesired by-products being obtained and which can be easily separated from the reaction mixture.

The aryl aliphatic ketones K may be separated from the reaction mixture by convenient and economic processes and the catalytic material can be used for several catalytic cycles without significant deterioration of catalytic activity.

As thoroughly shown, the aryl aliphatic ketones K are versatile starting materials that can be easily converted into a variety of valuable end compounds through the process P'.

The process P' of the present invention, since it is based on the process P, thus likewise offers an easier access to these compounds.

Many end compounds obtainable by the process P' are useful as surfactants.

Many other compounds obtainable by the process P' are useful as intermediates that can in turn be converted into valuable end compounds like surfactants.

Should the disclosure of any patents, patent applications, and publications which are incorporated herein by reference conflict with the description of the present application to the extent that it may render a term unclear, the present description shall take precedence.

The following examples further explain the present invention.

EXAMPLES

All the reactions were conducted under a strictly oxygen-free atmosphere (under argon).

1-Preparation of Phenylhexadecan-1-One:

1.1 Using 0.37 Equivalent of Benzoic Acid and 1 Equivalent of Palmitic Acid:

In a round bottom flask equipped with a Dean-Stark apparatus, an insulated addition funnel filled with 50 g of melted palmitic acid (195.1 mmol), a second solid addition funnel filled with 8.6 g of benzoic acid (70.5 mmol), a temperature probe and a mechanical stirrer are added 2 g of metal iron (35.8 mmol).

Initial complex generation and decomposition:

Then, 12.5 g (48.8 mmol) of palmitic acid followed by 2.9 g (23.8 mmol) of benzoic acid are added into the reaction medium and the mixture is allowed to stir at 250° C. during 2 h. As it can be easily calculated, the amount of iron used in this first step corresponds nearly to half of the sum of the number of moles of palmitic acid and the number of moles of benzoic acid.

During this first step, $Fe^{(0)}$ is converted to a mixture of $Fe^{(II)}$ carboxylate complexes with concomitant release of hydrogen gas. After complete conversion of acids toward complexes (that can be followed thanks to FTIR analysis), the reaction media is heated to 315° C. and allowed to stir at this temperature during 1h30 in order to complete the transformation of complexes II and III toward the corresponding ketones. Release of $CO_2$ gas is observed at this stage.

Cycles of acid addition and ketonization:

Thereafter, 1.9 g of benzoic acid (15.6 mmol) and 12.5 g of palmitic acid (48.8 mmol) are added into the reactor and the mixture is allowed to stir at 315° C. The reaction progress can be followed by FTIR analysis which showed that conversion of the complexes toward ketones was achieved after 1h15 of reaction time after the end of the addition.

Two additional cycles each consisting of acids addition (12.5 g of palmitic acid and 1.9 g of benzoic acid) followed by heating at 315° C. during 1h15 min were performed.

Finally, the reaction progress was monitored thanks to FTIR in order to ensure that complete conversion of complexes II and III was reached. This requires usually an additional 0h30 of stirring after the last cycle.

Work-up:

After reaction completion, the reaction mixture is cooled down at 40° C. and chloroform ($CHCl_3$) is added into the mixture to dissolve products. In order to separate the desired product from iron oxide and the remaining iron carboxylate complex, the chloroform mixture is filtered over a silica plug and the product eluted with around 1.5 L of $CHCl_3$. After evaporation of the solvent, 47.71 g of product (91% yield relative to fatty acids) is obtained as a light brown powder constituted of 55 mol % of phenylhexadecan-1-one and 45 mol % of hentriacontan-16-one (palmitone).

One can easily determine in theory by calculation the number of moles of palmitic acid and the number of moles of benzoic acid that have been consumed and converted into ketones during each decomposition phase of complexes II and III. The calculation will be provided hereunder. A similar calculation may be made for all the other examples.

The ratio of the number of moles of aryl carboxylic acid (benzoic acid) to the number of aliphatic carboxylic acid (palmitic acid) introduced during the first step of complex generation is 23.8 mmol/48.8 mmol-0.5 which means that 0.5 equivalent of benzoic acid is used for 1 equivalent of palmitic acid.

Table 1 above indicates at row entitled "condition 1" that for a ratio aryl carboxylic acid/aliphatic carboxylic acid of 0.5/1, the following equivalents are formed:

0.08 equivalent of the diaromatic complex (complex I) is formed;
0.33 equivalent of the aryl aliphatic complex (complex II) is formed;
0.33 equivalent of the dialky complex (complex III) is formed.

We can then calculate the number of moles of each complex formed knowing that 1 equivalent represents in this case 48.8 mmol.

0.08×48.8=3.90 mmol of the diaromatic complex (complex I) are formed;
0.33×48.8=16.27 mmol of the aryl aliphatic complex (complex II) are formed;
0.33×48.8=16.27 mmol equivalent of the dialiphatic complex (complex III) is formed.

The formation of 1 mole of the aryl aliphatic complex (complex II) requires 1 mole of aryl carboxylic acid and 1 mole of aliphatic carboxylic acid.

The formation of 1 mole of the dialiphatic complex (complex III) requires 2 moles of aliphatic carboxylic acid.

Complex I does not decompose into a ketone.

One can thus determine that the formation 16.27 mmol of the aryl aliphatic ketone has required 16.27 mmol of aryl carboxylic acid and 16.27 mmol of aliphatic carboxylic acid.

One can also determine that the formation 16.27 mmol of the dialiphatic ketone has required 2×16.27=32.54 mmol of aliphatic carboxylic acid.

One finds that the number of moles of aryl carboxylic acid that was converted into the aryl aliphatic ketone was 16.27 mmol.

One finds that the number of moles of aliphatic carboxylic acid that was consumed to form the aryl aliphatic ketone and the dialiphatic ketone was 32.54+16.27=48.8 mmol meaning the entire amount of aliphatic carboxylic acid introduced during the step of complex generation and decomposition.

The experimental amounts of 15.6 and 48.8 mmol used during each cycle of step 2 in the above example are consistent with these two theoretical values of 16.27 and 48.8 mmol.

1.2 Using 0.83 Equivalent of Benzoic Acid and 1 Equivalent of Palmitic Acid:

The reaction is carried out following the protocol described in Example 1.1 with a total amount of 50 g of palmitic acid (195.1 mmol), 19.8 g of benzoic acid (162.2 mmol) and 3.4 g of $Fe^{(0)}$ (60.8 mmol).

During initial complex generation and decomposition, 3.4 g (60.8 mmol) of Fe is reacted with 12.5 g (48.8 mmol) of palmitic acid and 9.0 g (73.7 mmol) of benzoic acid.

During the 3 cycles of acids addition and decomposition, 12.5 g (48.8 mmol) of palmitic acid and 3.6 g (29.5 mmol) of benzoic acid are added at each cycle.

The product is obtained as a brown powder (51.84 g, 91% isolated yield relative to the fatty acid) and consists of 85 mol % of aryl aliphatic ketone and 15 mol % of hentriacontan-16-one.

1.3 Using 1.75 Equivalent of Benzoic Acid and 1 Equivalent of Palmitic Acid:

The reaction is carried out following the protocol described in Example 1.1 with a total amount of 32.8 g of palmitic acid (128.0 mmol), 27.2 g of benzoic acid (222.9 mmol) and 4.9 g of Fe (87.6 mmol).

During initial complex generation and decomposition, 4.9 g (87.6 mmol) of Fe is reacted with 8.2 g (32.0 mmol) of palmitic acid and 17.6 g (144.2 mmol) of benzoic acid.

During the 3 cycles of acids addition and decomposition, 8.2 g (32.0 mmol) of palmitic acid and 3.2 g (26.2 mmol) of benzoic acid are added at each cycle.

The product is obtained as a brown powder (33.75 g, 83% isolated yield relative to the fatty acid) and consists of 99 mol % of cross adduct and only 1 mol % of hentriacontan-16-one.

2-Preparation of 1-Phenyldodecan-1-One:

2.1 Using 0.83 Equivalent of Benzoic Acid and 1 Equivalent of Lauric Acid:

The reaction is carried out following the protocol described in Example 1.1 with a total amount of 39.2 g of lauric acid (195.8 mmol), 19.8 g of benzoic acid (162.2 mmol) and 3.4 g of $Fe^{(0)}$ (60.8 mmol).

During initial complex generation and decomposition, 3.4 g (60.8 mmol) of Fe is reacted with 9.8 g (48.9 mmol) of lauric acid and 9.0 g (73.7 mmol) of benzoic acid.

During the 3 cycles of acids addition and decomposition, 9.8 g (48.9 mmol) of lauric acid and 3.6 g (29.5 mmol) of benzoic acid are added at each cycle.

The product is obtained as a brown powder (40.3 g, 87% isolated yield relative to the fatty acid) and consists of 87 mol % of cross adduct and 13 mol % of tricosan-12-one.

2.2 Using 1.75 Equivalent of Benzoic Acid and 1 Equivalent of Lauric Acid:

The reaction is carried out following the protocol described in Example 1.1 with a total amount of 25.6 g of lauric acid (127.9 mmol), 27.2 g of benzoic acid (222.9 mmol) and 4.9 g of Fe$^{(0)}$ (87.6 mmol).

During initial complex generation and decomposition, 4.9 g (87.6 mmol) of Fe is reacted with 6.4 g (31.9 mmol) of lauric acid and 17.6 g (144.2 mmol) of benzoic acid.

During the 3 cycles of acids addition and decomposition, 6.4 g (31.9 mmol) of lauric acid and 3.2 g (26.2 mmol) of benzoic acid are added at each cycle.

The product is obtained as a brown powder (23.84 g, 71% isolated yield relative to the fatty acid) and consists of 99 mol % of cross adduct and 1 mol % of tricosan-12-one.

The reaction is carried out following the protocol described in Example 1.1 with a total amount of 39.2 g of lauric acid (195.8 mmol), 18.1 g of 3-furoic acid (161.9 mmol) and 3.4 g of Fe (60.8 mmol).

During initial complex generation and decomposition, 3.4 g (60.8 mmol) of Fe is reacted with 9.8 g (48.9 mmol) of lauric acid and 8.2 g (73.2 mmol) of furoic acid.

During the 3 cycles of acids addition and decomposition, 9.8 g (48.9 mmol) of lauric acid and 3.3 g (29.5 mmol) of furoic acid are added at each cycle.

The product is obtained as a black viscous oil (36.5 g, 91% isolated yield relative to the fatty acid) and consists of 58 mol % of cross adduct and 42 mol % of tricosan-12-one.

The results in terms of isolated yields and selectivity obtained for the above examples are summarized in the following table:

TABLE 2

Values of yields and selectivities

| Example | Aromatic acid | Fatty acid | % mol Fe (% wt.) | Molar ratio aromatic acid:fatty acid | Yield % in ketone | Selectivity (mol % of aryl aliphatic ketone) |
|---|---|---|---|---|---|---|
| .1 | benzoic acid | palmitic acid | 13 (3.4) | 0.37:1 | 91 | 55 |
| 1.2 | benzoic acid | palmitic acid | 17 (4.9) | 0.83:1 | 91 | 85 |
| 1.3 | benzoic acid | palmitic acid | 25 (8.2) | 1.75:1 | 83 | 99 |
| 2.1 | benzoic acid | lauric acid | 17 (5.8) | 0.83:1 | 87 | 87 |
| 2.2 | benzoic acid | lauric acid | 25 (9.3) | 1.75:1 | 71 | 99 |
| 3.1 | 2-furoic acid | lauric acid | 17 (5.9) | 0.83:1 | 80 | 24 |
| 3.2 | 2-furoic acid | lauric acid | 24 (9.3) | 1.75:1 | 91 | 49 |
| 4.1 | 3-furoic acid | lauric acid | 17 (5.9) | 0.83:1 | 91 | 58 |

3-Preparation of 1-(Furan-2-Yl)Dodecan-1-One:
3.1 Using 0.83 Equivalent of 2-Furoic Acid and 1 Equivalent of Lauric Acid:

The reaction is carried out following the protocol described in Example 1.1 with a total amount of 39.2 g of lauric acid (195.8 mmol), 18.1 g of 2-furoic acid (161.6 mmol) and 3.4 g of Fe (60.8 mmol).

During initial complex generation and decomposition, 3.4 g (60.8 mmol) of Fe$^{(0)}$ is reacted with 9.8 g (48.9 mmol) of lauric acid and 8.2 g (73.2 mmol) of 2-furoic acid.

During the 3 cycles of acids addition and decomposition, 9.8 g (48.9 mmol) of lauric acid and 3.3 g (29.5 mmol) of 2-furoic acid are added at each cycle.

The product is obtained as a black viscous oil (23.84 g, 80% isolated yield relative to the fatty acid) and consists of 24 mol % of cross adduct and 76 mol % of tricosan-12-one.

3.2 Using 1.75 Equivalent of 2-Furoic Acid and 1 Equivalent of Lauric Acid:

The reaction is carried out following the protocol described in Example 1.1 with a total amount of 25.6 g of lauric acid (127.9 mmol), 25.5 g of 2-furoic acid (228.0 mmol) and 4.91 g of Fe (87.8 mmol).

During initial complex generation and decomposition, 4.91 g (87.8 mmol) of Fe is reacted with 6.4 g (31.9 mmol) of lauric acid and 16.1 g (144.0 mmol) of 2-furoic acid.

During the 3 cycles of acids addition and decomposition, 6.4 g (31.9 mmol) of lauric acid and 3.1 g (27.7 mmol) of 2-furoic acid are added at each cycle.

The product is obtained as a black viscous oil (22.96 g, 91% isolated yield relative to the fatty acid) and consists of 49 mol % of cross adduct and 51 mol % of tricosan-12-one.

4-Preparation of 1-(Furan-3-Yl)Dodecan-1-One:
4.1 Using 0.83 Equivalent of 3-Furoic Acid and 1 Equivalent of Lauric Acid:

5-Control Experiment:
Stoichiometric Reaction Between Fe-(Laurate)$_2$ Complex and Fe-(Benzoate)$_2$ Complex:

Preparation of Fe-laurate complex:

In a 50 mL round bottom flask equipped with a magnetic stirrer, under an inert argon atmosphere, 1.8 g of Fe (32.2 mmol) is reacted at 240° C. with 12.5 g of lauric acid (62.4 mmol). The reaction is monitored thanks to FTIR analysis. When complete conversion of fatty acid toward the desired complex is observed, the reaction mixture is cooled down at room temperature and the product is washed several times with acetone in order to remove traces of remaining acid, ketone and by-products.

8.62 g of complex has been obtained as a brown powder (61% yield).

Preparation of Fe-benzoate complex:

In a 50 mL round bottom flask equipped with a magnetic stirrer, under an inert argon atmosphere, 1.8 g of Fe (32.2 mmol) is reacted at 250° C. with 7.6 g of benzoic acid (62.3 mmol). The reaction is monitored thanks to FTIR analysis. When complete conversion of benzoic acid toward the desired complex is observed the reaction mixture is cooled down at room temperature and the product is washed several times with acetone in order to remove traces of remaining acid and by-products.

4.33 g of complex has been obtained as a brown powder (47% yield).

Stoichiometric reaction between the aromatic complex and the aliphatic complex:

In a 50 mL round bottom flask equipped with a mechanical stirrer, under an inert argon atmosphere, 4.3 g of Fe-benzoate complex (62.3 mmol) is reacted at 315° C. with 6.6 g of Fe-laurate complex (62.3 mmol). The reaction is monitored thanks to FTIR analysis.

At the end of the reaction, when complete conversion of complex toward ketones has been observed, the reaction mixture is cooled down at 40° C. and $CHCl_3$ is added into the mixture to dissolve products.

In order to separate the desired product from iron oxide and remaining iron carboxylate complex, the chloroform mixture is filtered over a silica plug and the product eluted with around 1.5 L of $CHCl_3$. After evaporation of the solvent, 5.41 g of product (77% yield) is obtained as a light brown powder constituted of 86 mol % of 1-phenyldodecan-1-one and 14 mol % of tricosan-12-one.

This control experiment shows that:
1) Carboxylate ligands exchange around Fe center is rapid in the conditions of the invention and faster than the ketonization step that converts Fe complexes toward the ketones.
2) Selectivity in this 1:1 stoichiometric reaction between lauric acid and benzoic acid is 86%. In comparison, a similar selectivity has been obtained in the present invention using only 0.83 equivalent of benzoic acid versus aliphatic acid showing that under this implementation, selectivity toward the aryl aliphatic ketone is improved using catalytic quantities of Fe.

The invention claimed is:

1. A process for the catalytic decarboxylative cross-ketonisation of aryl- and aliphatic carboxylic acids comprising the steps of:
   a) providing a mixture containing:
      i) an aryl carboxylic acid;
      ii) an aliphatic carboxylic acid;
      iii) a metal-containing compound;
      in which the number of moles of the metal in the mixture is at least equal to 90% of the sum of the number of moles of aryl carboxylic acid and the number of moles of aliphatic carboxylic acid divided by the valency of the metal
      said mixture being substantially free of any added solvent;
   b) heating the mixture at a temperature sufficient to form metal carboxylates;
   c) further heating the mixture at a temperature sufficient to form a dialiphatic ketone and an aryl aliphatic ketone K;
   d) adding to the reaction mixture of step c):
      i) aryl carboxylic acid in an amount which corresponds substantially to the amount of aryl carboxylic acid consumed during the formation of the aryl aliphatic ketone K in step c);
      ii) aliphatic carboxylic acid in an amount which corresponds substantially to the amount of aliphatic carboxylic acid consumed during the formation of the aryl aliphatic ketone K and the dialiphatic ketone in step c);
      maintaining the mixture at a temperature sufficient to continue forming the dialiphatic ketone and the aryl aliphatic ketone K;
   e) optionally repeating step d).

2. The process of claim 1, wherein:
   x is the number of moles of aryl carboxylic acid
   y is the number of moles of aliphatic carboxylic acid, and
   the number of moles of a metal of valence z in the mixture of step a) is within the range of from $0.9[(x+y)/z]$ to $1.1[(x+y)/z]$.

3. The process according to claim 1, wherein the metal is iron-containing compound.

4. The process of claim 3, wherein the iron-containing compound is selected from the group consisting of iron metal, bivalent $Fe^{(II)}$ compounds, trivalent $Fe^{(III)}$ compounds, and compounds in which iron is present in both bivalent $Fe^{(II)}$ and bivalent $Fe^{(III)}$ oxidation states.

5. The process of claim 1, wherein step b) is carried out at a temperature $T_1$ from 225° C. to 290° C., and steps c) and step d) are carried out at a temperature $T_2$ from 300° C. to 400° C.

6. The process of claim 1, wherein the molar ratio of the total amount of aryl carboxylic acid and the aliphatic carboxylic acid ranges from 0.3 to 1.8.

7. The process of claim 1, wherein the aryl carboxylic acid is selected from the group consisting of benzoic acid, furoic acid, o-toluic acid, m-toluic acid and p-toluic acid.

8. The process of claim 1, wherein the aliphatic carboxylic acid is a fatty acid.

9. The process according to claim 8, wherein the fatty acid contains from 8 to 18 carbon atoms.

10. A process for the preparation of at least one end compound from at least one aryl aliphatic ketone K, said process comprising:
   synthesizing the aryl aliphatic ketone K through the process of claim 1,
   causing the aryl aliphatic ketone K to react in accordance with a single or multiple chemical reaction scheme involving at least one reagent other than the aryl aliphatic ketone K, wherein at least one product of the chemical reaction scheme is the end compound product that is not further caused to be chemically converted into another compound.

* * * * *